United States Patent
Hoyer et al.

(10) Patent No.: US 12,064,415 B2
(45) Date of Patent: *Aug. 20, 2024

(54) PSILOCIN PRODRUG COMPOUNDS AND METHODS OF SYNTHESIZING THE SAME

(71) Applicant: Mydecine Innovations Group Inc., Denver, CO (US)

(72) Inventors: Denton W. Hoyer, West Haven, CT (US); Robert F. Roscow, Longmont, CO (US)

(73) Assignee: MYDECINE INNOVATIONS GROUP INC., Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/142,263

(22) Filed: May 2, 2023

(65) Prior Publication Data

US 2023/0364058 A1 Nov. 16, 2023

Related U.S. Application Data

(63) Continuation-in-part of application No. PCT/US2023/019714, filed on Apr. 25, 2023.

(60) Provisional application No. 63/340,067, filed on May 10, 2022.

(51) Int. Cl.
| | | |
|---|---|---|
| *C07D 471/04* | (2006.01) | |
| *A61K 31/4045* | (2006.01) | |
| *A61K 31/437* | (2006.01) | |

(52) U.S. Cl.
CPC ........ *A61K 31/4045* (2013.01); *A61K 31/437* (2013.01)

(58) Field of Classification Search
CPC .. C07D 471/04; C07D 209/16; A61K 31/437; A61K 31/404
USPC .................. 546/113; 548/484; 514/300, 415
See application file for complete search history.

(56) References Cited

U.S. PATENT DOCUMENTS

2018/0221396 A1   8/2018   Chadeayne

FOREIGN PATENT DOCUMENTS

| WO | 2014018888 A1 | 1/2014 | |
|---|---|---|---|
| WO | 2014033597 A1 | 3/2014 | |
| WO | 2020245133 A1 | 12/2020 | |
| WO | 2021116503 A2 | 6/2021 | |
| WO | 2021155470 A1 | 8/2021 | |
| WO | 2022026223 A1 | 2/2022 | |
| WO | 2022038299 A1 | 2/2022 | |
| WO | WO 2022/038299 A1 * | 2/2022 | ........... C07D 209/16 |

OTHER PUBLICATIONS

Pubchem, Substance Record for SID 255918009, Modify Date: Aug. 25, 2017 [retrieved on Jan. 25, 2022]. Retrieved from the Internet: <URL: https://pubchem.ncbi.nlm.nih.gov/substance/255918009>. entire document.
Pubchem CID 53412486, Create date: Oct. 30, 2011 (Oct. 30, 2011), entire document, especially p. 2, compound listed.
Malaca et al., "Toxicology and Analysis of Psychoactive Tryptamines", International Journal of Molecular Scinces, Dec. 4, 2020 (Dec. 4, 2020), 21, 9279, pp. 1-30, entire document, especially p. 1, abstract, para 1; p. 2, para 5; Table 1; Figure 1.
Giorgetti et al.. "Detection and phase I metabolism of the 7?azaindole derlved synthetic cannabinold 5F-AB-P7 AICA Including a preliminary pharmacokinelic evaluation", Drug Testing and Analysis, Sep. 2, 2019 (Sep. 2, 2019), 12, pp. 78-91, entire document, especially p. 78, abstract; Figures 1, 4.
ZINC44713096, Create date: Jul. 21, 2010 (Jul. 21, 2010), entire document, especially p. 1.
International Search Report and Written Opinion in PCT/US21/61826 with mailing date of Apr. 11, 2022, 11 pages.
International Search Report and Written Opinion in PCT/US22/31945 with mailing date of Nov. 7, 2022, 80 pages.

* cited by examiner

*Primary Examiner* — Charanjit Aulakh
(74) *Attorney, Agent, or Firm* — Berg Hill Greenleaf Ruscitti LLP

(57) ABSTRACT

The present invention includes a novel class of psilocin carbamates and carbonate prodrug compounds having one or more aza substitution within the psilocin core. The psilocin prodrugs of the invention are enzymatically cleaved in vivo.

16 Claims, No Drawings

PSILOCIN PRODRUG COMPOUNDS AND METHODS OF SYNTHESIZING THE SAME

CROSS-REFERENCE TO RELATED APPLICATIONS

This application is a U.S. Continuation-in-part of Application No. PCT/US23/19714 having an international filing date of Apr. 25, 2023, which designated the United States, which PCT application claimed the benefit of U.S. Provisional Application No. 63/340,067 filed May 10, 2022, the specification, claims and drawings of which are incorporated herein by reference in their entirety.

TECHNICAL FIELD

The present invention is directed to novel chemical compositions of matter, and in particular novel psilocin prodrug compounds, and in particular novel psilocin carbonate and/or carbamate prodrug compounds, further including novel psilocin carbonate and/or carbamate prodrug compounds containing one or more aza substitutions.

BACKGROUND

The serotonin 2A receptor (5-HT2A) has been implicated in mental disorders with complex etiologies that are still not clearly understood, in processes such as learning and memory and also in neurogenesis. The tryptamine compounds psilocybin and psilocin are known agonists of the 5-HT2A serotonin receptor. Activation of this receptor has been shown to provide benefit in therapies that address mental health disorders. The present invention addresses this need and provides novel psilocin carbamates and carbonate prodrug compounds having one or more aza substitution within the psilocin core. The psilocin prodrugs of the invention are enzymatically cleaved in vivo, and may exhibit improved properties, such as improved duration of action for therapeutic dosing in clinical settings, as well as enhanced lipophilicity which render them highly advantageous for therapeutic use.

SUMMARY OF THE INVENTION

The present invention includes novel psilocin prodrug carbamates and carbonate prodrug compounds having one or more aza substitution in the psilocin core ring structure. In a preferred aspect, the novel psilocin prodrug compounds may include the compounds of Formulas I-XI, (also referred to as a/the compound(s) or composition(s) of the invention, or psilocin prodrug), or a pharmaceutically acceptable salt, solvate, stereoisomer, tautomer, or prodrug thereof as described herein.

In another aspect, the present invention includes a novel psilocin prodrug compounds according to Formula I-XI as described herein. Additional aspects of the present invention provides a systems, methods, and compositions for novel psilocin prodrug compounds according to the compounds of Formula I-XI, and a pharmaceutically acceptable carrier or diluent, which may preferably further include a method of treatment of the human or animal body using one or more of the novel psilocin prodrug compounds, or pharmaceutical compositions described herein.

Additional aspects of the present invention provide a method for treating a disease or condition for which modulation of serotonin receptor activity is beneficial comprising: administering to a subject in need thereof, a therapeutically effective amount of a one or more compounds of the invention, or a pharmaceutically acceptable composition, also generally referred to as a pharmaceutical composition or a pharmaceutical composition of the invention containing a therapeutically effective amount of a one or more compounds of the invention and a pharmaceutically carrier. In another aspect, the present invention include novel prodrug modifications to psilocin configured to facilitate transdermal delivery of the compound.

Additional aspects of the present invention provide a method for treating a disease or condition for which modulation of serotonin receptor activity is beneficial comprising: administering to a subject in need thereof, a therapeutically effective amount of a one or more compounds of the invention, or a pharmaceutically acceptable composition, also generally referred to as a pharmaceutical composition or a pharmaceutical composition of the invention containing a therapeutically effective amount of a one or more compounds of the invention and a pharmaceutically carrier. In another aspect, the present invention include novel prodrug modifications to psilocin configured to facilitate transdermal delivery of the compound.

Additional aspects of the invention may become evident based on the specification and figures presented below.

DETAILED DESCRIPTION OF THE INVENTION

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

The present invention includes novel psilocin carbamates and carbonate prodrug compounds having one or more aza substitution in the psilocin core ring structure. As shown below, the compounds of Formulas I-XI describe novel psilocin carbamates and carbonate prodrug compounds having one or more aza substitution in the psilocin core ring structure, and specifically one or more N or aza substitutions to their Azaindole group. The carbon to nitrogen replacement in the psilocin prodrug may increase oxidation potential such that the degradation by oxygen is inhibited. This can be measured by calculating the HOMO energies of the prodrug compounds of the invention compared to the parent psilocin and more specifically by an "average local ionization energy" analysis. The more aza substitutions in the psilocin prodrug may also affect the degree to which glucuronidation occur, which is a major metabolic route of elimination from the body. For example, the prodrugs compounds of the invention having an aza substitution in their azaindole group, may have reduced glucuronidation and therefore slowed excretion.

In a preferred embodiment, the invention includes a psilocin prodrug compound having at least one aza substitution, and a carbamates and carbonate group as described herein. In one preferred embodiment, the invention includes a psilocin prodrug compound according to Formula I:

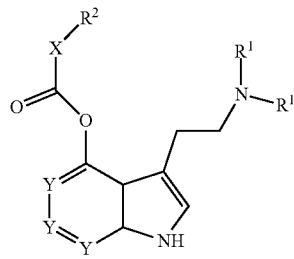

(I)

In this preferred embodiment Y is independently N or CH, wherein at least one Y is N; X is O, N, or NH; $R^1$ is alkyl or alkane; and $R^2$ is alkane; or a pharmaceutically acceptable salt thereof. In another preferred embodiment, the invention includes a psilocin prodrug compound according to Formula I, wherein: Y is independently N or CH, wherein at least one Y is N; X is O; $R^1$ is $CH_3$, or $CH(CH_3)_2$; and $R^2$ is $C_1$-$C_{14}$ linear alkane; or a pharmaceutically acceptable salt thereof.

In another preferred embodiment, the invention includes a psilocin prodrug compound according to Formula I, wherein: Y is independently N or CH, wherein at least one Y is N; X is O; $R^1$ is $CH_3$; and $R^2$ is selected from methyl, ethyl, n-proply, n-butyl, n-pentyl, n-hexyl, n-heptyl, n-octyl, n-nonyl, n-decyl, n-undecanyl, n-dodecanyl, n-tridecanyl, n-tertadecanyl; or a pharmaceutically acceptable salt thereof.

In a preferred embodiment, the invention includes a psilocin prodrug compound according to Formula II:

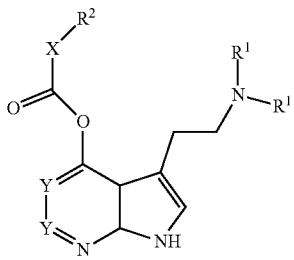

(II)

In this preferred embodiment Y is CH; X is O; $R^1$ is $CH_3$, or $CH(CH_3)_2$; and $R^2$ is $C_1$-$C_{14}$ linear alkane, or alkyl; or a pharmaceutically acceptable salt thereof. In another preferred embodiment, the invention includes a psilocin prodrug compound according to Formula II, wherein: Y is CH; X is O; $R^1$ is $CH_3$; and $R^2$ is selected from methyl, ethyl, n-proply, n-butyl, n-pentyl, n-hexyl, n-heptyl, n-octyl, n-nonyl, n-decyl, n-undecanyl, n-dodecanyl, n-tridecanyl, n-tertadecanyl; or a pharmaceutically acceptable salt thereof.

In a preferred embodiment, the invention includes a psilocin prodrug compound according to Formula III:

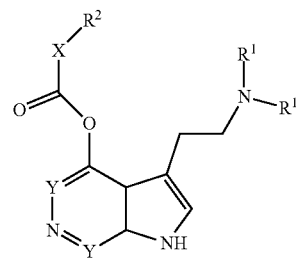

(III)

In this preferred embodiment Y is CH; X is O; $R^1$ is $CH_3$, or $CH(CH_3)_2$; and $R^2$ is $C_1$-$C_{14}$ linear alkane, or alkyl; or a pharmaceutically acceptable salt thereof. In another preferred embodiment, the invention includes a psilocin prodrug compound according to Formula III, wherein: Y is CH; X is O; $R^1$ is $CH_3$; and $R^2$ is selected from methyl, ethyl, n-proply, n-butyl, n-pentyl, n-hexyl, n-heptyl, n-octyl, n-nonyl, n-decyl, n-undecanyl, n-dodecanyl, n-tridecanyl, n-tertadecanyl; or a pharmaceutically acceptable salt thereof.

In a preferred embodiment, the invention includes a psilocin prodrug compound according to Formula IV:

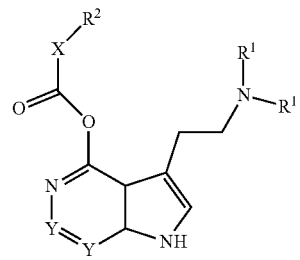

(IV)

In this preferred embodiment Y is CH; X is O; $R^1$ is $CH_3$, or $CH(CH_3)_2$; and $R^2$ is $C_1$-$C_{14}$ linear alkane, or alkyl; or a pharmaceutically acceptable salt thereof. In another preferred embodiment, the invention includes a psilocin prodrug compound according to Formula IV, wherein: Y is C; X is O; $R^1$ is $CH_3$; and $R^2$ is selected from methyl, ethyl, n-proply, n-butyl, n-pentyl, n-hexyl, n-heptyl, n-octyl, n-nonyl, n-decyl, n-undecanyl, n-dodecanyl, n-tridecanyl, n-tertadecanyl; or a pharmaceutically acceptable salt thereof.

In a preferred embodiment, the invention includes a psilocin prodrug compound according to Formula V:

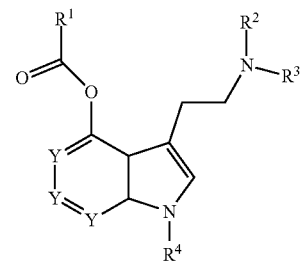

(V)

In this preferred embodiment Y is independently N or CH, wherein at least one X is N;

R¹ is selected from —O—(C$_{1-14}$ alkyl), —O—(C$_{1-14}$ alkane), —O—CH$_2$-phenyl, —CH$_2$—NH$_2$, —CH(—NH$_2$)—CH$_3$, —CH(—NH$_2$)—CH(—CH$_3$)—CH$_3$, —CH(—NH$_2$)—CH$_2$—CH(—CH$_3$)—CH$_3$, —CH(—NH$_2$)—CH(—CH$_3$)—CH$_2$CH$_3$, —CH(—NH$_2$)—CH$_2$—S—CH$_3$, —CH(—NH$_2$)—CH$_2$—SH, —CH(—NH$_2$)—CH$_2$—OH, —CH(—NH$_2$)—CH(—CH$_3$)—OH, —CH(—NH$_2$)—CH$_2$—C(═O)—NH$_2$, —CH(—NH$_2$)—CH$_2$CH$_2$—C(═O)—NH$_2$, —CH(—NH$_2$)—CH$_2$—COOH, —CH(—NH$_2$)—CH$_2$CH$_2$—COOH, —CH(—NH$_2$)—CH$_2$CH$_2$CH$_2$CH$_2$—NH$_2$, —CH(NH$_2$)—CH$_2$CH$_2$CH$_2$—NH—C(═NH)—NH$_2$, —CH(—NH$_2$)—CH$_2$-(1H-imidazol-4-yl), —CH(—NH$_2$)—CH$_2$-phenyl, —CH(—NH$_2$)—CH$_2$-(4-hydroxyphenyl), —CH(—NH$_2$)—CH$_2$-(1H-indol-3-yl), -(pyrrolidin-2-yl), -(4-hydroxypyrrolidin-2-yl), —CH(—NH$_2$)—CH$_2$—S—S—CH$_2$—CH(—NH$_2$)—COOH, —CH(—NH$_2$)—CH$_2$CH$_2$CH$_2$—NH$_2$, —CH(—NH$_2$)—CH$_2$CH$_2$CH$_2$—NH—C(═O)—NH$_2$, —CH$_2$—NH—CH$_3$, —CH(—NH$_2$)—CH$_2$CH$_2$—SH, —CH(—NH$_2$)—CH$_2$CH$_2$—OH, —CH(—NH$_2$)—CH$_2$-(3,4-dihydroxyphenyl), —CH(—NH$_2$)—CH$_2$-(5-hydroxy-1H-indol-3-yl), —CH$_2$CH$_2$—NH$_2$, —CH$_2$CH$_2$CH$_2$—NH$_2$, —CH(—CH$_3$)—CH$_2$—NH$_2$, —C(—NH$_2$)═CH$_2$, —O-(1-[R⁴]-3-[(—CH$_2$CH$_2$—N(—R²)—R³)]-1H-indol-4-yl), —O—(C$_{1-14}$ alkylene)-O-(1-[R⁴]-3-[(—CH$_2$CH$_2$—N(—R²)—R³)]-1H-indol-4-yl), —CH(—NH$_2$)—CH$_2$—COO-(1-[R⁴]-3-[(—CH$_2$CH$_2$—N(—R²)—R³)]-1H-indol-4-yl), —CH(—NH$_2$)—CH$_2$CH$_2$—COO-(1-[R⁴]-3-[(—CH$_2$CH$_2$—N(—R²)—R³)]-1H-indol-4-yl), —CH(—NH$_2$)—CH$_2$—S—S—CH$_2$—CH(—NH$_2$)—COO-(1-[R⁴]-3-[(—CH$_2$CH$_2$—N(—R²)—R³)]-1H-indol-4-yl), —O-(5-(aminomethyl)isoxazol-3-yl), and —CH(—NH$_2$)-(3-hydroxy-isoxazol-5-yl);

In another preferred embodiment, the invention includes a psilocin prodrug compound according to Formula V, wherein: R² and R³ are each independently selected from hydrogen, methyl, ethyl, CH(CH$_3$)$_2$ provided that R² and R³ are not both hydrogen; and R⁴ is hydrogen or —C(═O)—O—(C$_{1-6}$ alkyl); or a pharmaceutically acceptable salt thereof.

In another preferred embodiment, the invention includes a psilocin prodrug compound according to Formula V, wherein: R¹ is selected from —O—(C$_{1-12}$ alkyl) or —O—CH$_2$-phenyl.

In another preferred embodiment, the invention includes a psilocin prodrug compound according to Formula V, wherein: R¹ is selected from —CH$_2$—NH$_2$, —CH(—NH$_2$)CH$_3$, —CH(—NH$_2$)—CH(—CH$_3$)—CH$_3$, —CH(—NH$_2$)—CH$_2$—CH(—CH$_3$)—CH$_3$, —CH(—NH$_2$)—CH(—CH$_3$)CH$_2$CH$_3$, —CH(—NH$_2$)CH$_2$CH$_2$—S—CH$_3$, —CH(—NH$_2$)—CH$_2$—SH, —CH(—NH$_2$)—CH$_2$—OH, —CH(—NH$_2$)—CH(—CH$_3$)—OH, —CH(—NH$_2$)—CH$_2$—C(═O)NH$_2$, —CH(—NH$_2$)—CH$_2$CH$_2$—C(═O)—NH$_2$, —CH(—NH$_2$)—CH$_2$—COOH, —CH(—NH$_2$)—CH$_2$CH$_2$—COOH, —CH(—NH$_2$)—CH$_2$CH$_2$CH$_2$CH$_2$—NH$_2$, —CH(—NH$_2$)—CH$_2$CH$_2$CH$_2$—NH—C(═NH)—NH$_2$, —CH(—NH$_2$)—CH$_2$-(1H-imidazol-4-yl), —CH(—NH$_2$)—CH$_2$-phenyl, —CH(—NH$_2$)—CH$_2$-(4-hydroxyphenyl), —CH(—NH$_2$)—CH$_2$-(1H-indol-3-yl), and -(pyrrolidin-2-yl).

In another preferred embodiment, the invention includes a psilocin prodrug compound according to Formula V, wherein: R¹ is selected from —CH(—NH$_2$)—CH(—CH$_3$)—CH$_3$, —CH(NH$_2$)—CH$_2$—CH(—CH$_3$)—CH$_3$, —CH(—NH$_2$)—CH(—CH$_3$)—CH$_2$CH$_3$, —CH(—NH$_2$)—CH$_2$CH$_2$—S—CH$_3$, —CH(—NH$_2$)—CH$_2$—SH, —CH(—NH$_2$)—CH$_2$—OH, —CH(—NH$_2$)—CH(—CH$_3$)—OH, —CH(—NH$_2$)—CH$_2$—C(═O)—NH$_2$, —CH(—NH$_2$)—CH$_2$CH$_2$—C(═O)NH$_2$, —CH(—NH$_2$)—CH$_2$—COOH, —CH(—NH$_2$)—CH$_2$CH$_2$—COOH, —CH(—NH$_2$)—CH$_2$CH$_2$CH$_2$CH$_2$—NH$_2$, —CH(—NH$_2$)CH$_2$CH$_2$CH$_2$—NH—C(═NH)—NH$_2$, —CH(—NH$_2$)—CH$_2$-(1H-imidazol-4-yl), —CH(—NH$_2$)—CH$_2$-phenyl, —CH(—NH$_2$)—CH$_2$-(4-hydroxyphenyl), —CH(—NH$_2$)—CH$_2$-(1H-indol-3-yl), and -(pyrrolidin-2-yl).

In another preferred embodiment, the invention includes a psilocin prodrug compound according to Formula V, wherein: R¹ is selected from -(4-hydroxypyrrolidin-2-yl), —CH(—NH$_2$)—CH$_2$—S—S—CH$_2$—CH(—NH$_2$)—COOH, —CH(—NH$_2$)—CH$_2$CH$_2$CH$_2$—NH$_2$, —CH(—NH$_2$)—CH$_2$CH$_2$CH$_2$—NHC(═O)—NH$_2$, —CH$_2$—NH—CH$_3$, —CH(—NH$_2$)—CH$_2$CH$_2$—SH, —CH(—NH$_2$)—CH$_2$CH$_2$—OH, —CH(—NH$_2$)—CH$_2$-(3,4-dihydroxyphenyl), —CH(—NH$_2$)—CH$_2$-(5-hydroxy-1H-indol-3-yl), —CH$_2$CH$_2$—NH$_2$, —CH$_2$CH$_2$CH$_2$—NH$_2$, —CH(—CH$_3$)CH$_2$—NH$_2$, and —C(—NH$_2$)═CH$_2$.

In another preferred embodiment, the invention includes a psilocin prodrug compound according to Formula V, wherein: R² and R³ are each methyl. In another preferred embodiment, the invention includes a psilocin prodrug compound according to Formula V, wherein: R² is methyl and R³ is hydrogen. In another preferred embodiment, the invention includes a psilocin prodrug compound according to Formula V, wherein: R² is methyl and R³ is ethyl. In another preferred embodiment, the invention includes a psilocin prodrug compound according to Formula V, wherein: R⁴ is hydrogen. In another preferred embodiment, the invention includes a psilocin prodrug compound according to Formula V, wherein: R⁴ is —C(═O)—O—(C$_{2-4}$ alkyl).

In a preferred embodiment, the invention includes a psilocin prodrug compound according to Formula V, wherein: Y is independently N or CH, wherein at least one X is N; R¹ is selected from —O—(C$_{1-14}$ alkyl), —O—CH$_2$-phenyl, —CH$_2$—NH$_2$, —CH(—NH$_2$)—CH$_2$—COOH, and —CH(—NH$_2$)—CH$_2$-(1H-indol-3-yl); R² is methyl or ethyl; R³ is methyl or ethyl; and R⁴ is H; or a pharmaceutically acceptable salt thereof. In another preferred embodiment, the invention includes a psilocin prodrug compound according to Formula V, R¹ is —O—(C$_{1-14}$ alkyl) or —O—CH$_2$-phenyl. In another preferred embodiment, the invention includes a psilocin prodrug compound according to Formula V, R¹ is selected from —CH$_2$—NH$_2$, —CH(—NH$_2$)—CH$_2$—COOH, and —CH(—NH$_2$)—CH$_2$-(1H-indol-3-yl). In another preferred embodiment, the invention includes a psilocin prodrug compound according to Formula V, R² and R³ are each methyl.

In a preferred embodiment, the invention includes a psilocin prodrug compound according to Formula VI (also referred to herein as MY276):

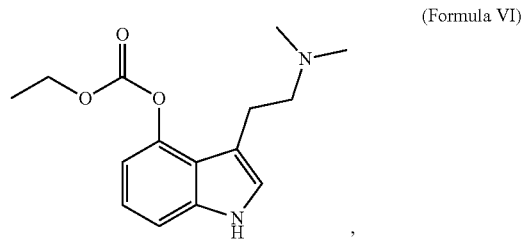 [SMILES: CCOC(=O)Oc1cccc2[nH]cc(CCN(C)C)c12]

(Formula VI)

or a pharmaceutically acceptable salt thereof.

In a preferred embodiment, the invention includes a psilocin prodrug compound according to Formula VII (also referred to herein as MY318):

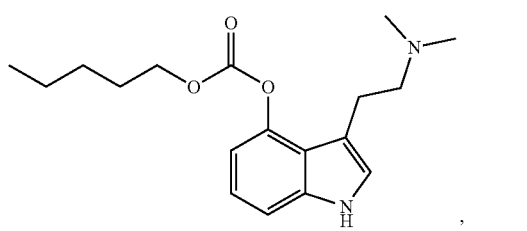

(Formula VII)

or a pharmaceutically acceptable salt thereof.

In a preferred embodiment, the invention includes a psilocin prodrug compound according to Formula VIII (also referred to herein as MY331):

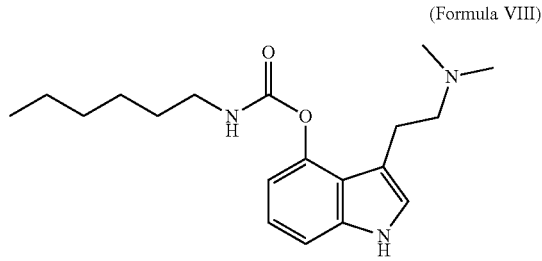 [SMILES: CCCCCCNC(=O)Oc1cccc2[nH]cc(CCN(C)C)c12]

(Formula VIII)

or a pharmaceutically acceptable salt thereof.

In a preferred embodiment, the invention includes a psilocin prodrug compound according to Formula IX (also referred to herein as MY332):

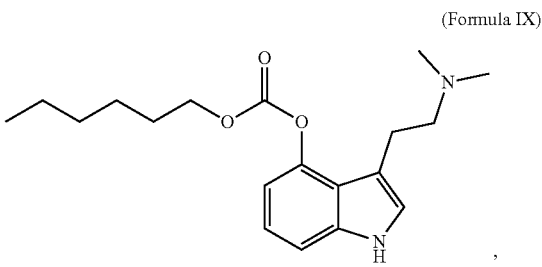 [SMILES: CCCCCCOC(=O)Oc1cccc2[nH]cc(CCN(C)C)c12]

(Formula IX)

or a pharmaceutically acceptable salt thereof.

In a preferred embodiment, the invention includes a psilocin prodrug compound according to Formula X (also referred to herein as MY333A):

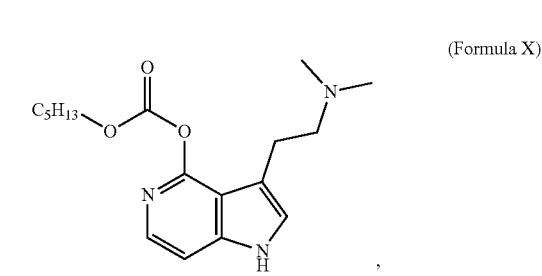

(Formula X)

or a pharmaceutically acceptable salt thereof.

In a preferred embodiment, the invention includes a psilocin prodrug compound according to Formula XI (also referred to herein as MY333B):

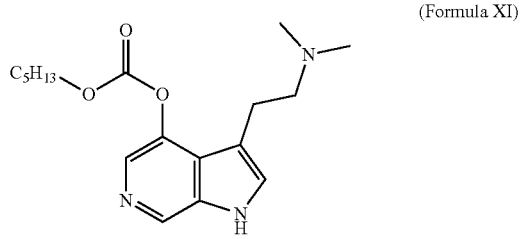

(Formula XI)

or a pharmaceutically acceptable salt thereof.

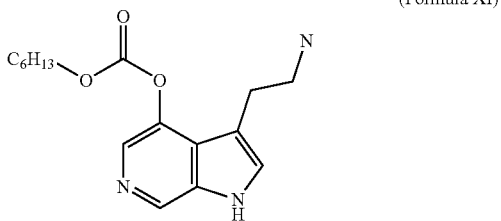

(Formula XI)

In a preferred embodiment, the invention includes a psilocin prodrug compound selected

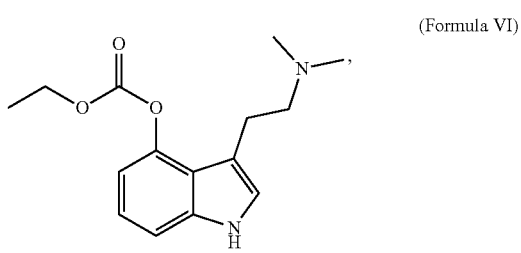 [SMILES: CCOC(=O)Oc1cccc2[nH]cc(CCN(C)C)c12]

(Formula VI)

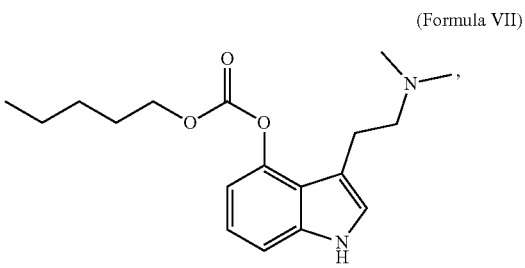 [SMILES: CCCCCOC(=O)Oc1cccc2[nH]cc(CCN(C)C)c12]

(Formula VII)

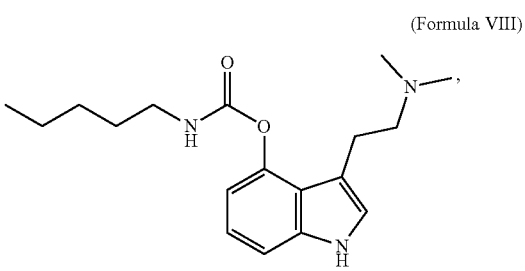

(Formula VIII)

(Formula IX)

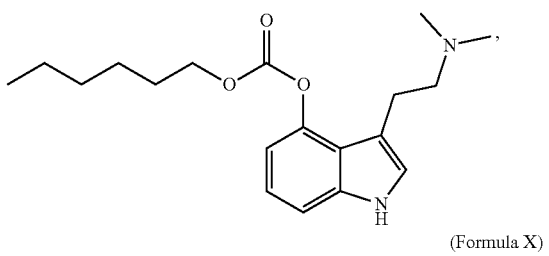

(Formula X)

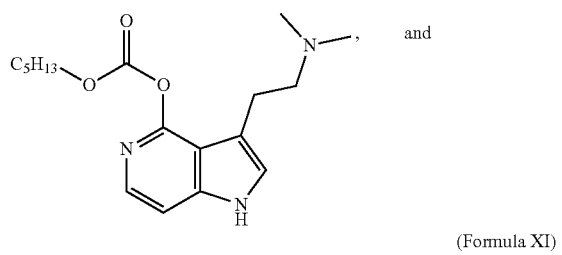

and (Formula XI)

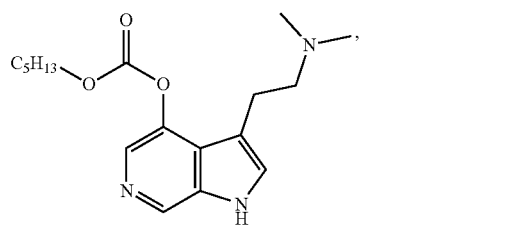

or a pharmaceutically acceptable salt thereof.

Additional embodiment may include a compound according to:

(Formula XII)

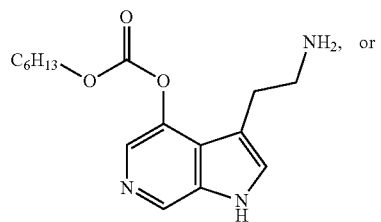

or (Formula XIII)

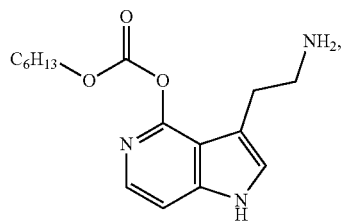

or a pharmaceutically acceptable salt thereof.

In another aspect, the psilocin prodrug compounds of the invention may exhibit increased enhance dermal permeation due to their high lipophilicity. Cleavage to the parent active psilocin may occur in the skin and/or liver. In this manner, the onset of psilocin action would be determined by the rate of permeation and release in the body. Further, the psilocin prodrug compounds of the invention allow onset of drug action from dermal application to be sustained at an even rate. This delivery strategy allows longer duration and avoidance of sudden $C_{max}$ serum concentrations.

In one aspect, the psilocin prodrug compounds of the invention dosed orally, which may delay action of the compound's effect on a subject, but can results in a longer duration of action from the parent dosed orally. This slower onset and more even distribution of the compound's action can be useful in preventing the illicit use of compounds of the invention as the delay in onset and more sustained action would discourage abuse. The action of the psilocin prodrug compounds of the invention can also allow easier formulation as a patch, may further provide for greater shelf stability and resistance to oxidation and degradation.

Method of synthesizing psilocin prodrugs lacking one or more aza substitution within the psilocin core are provided by the specification, and in particular Example 1-9, the materials and methods of PCT/EP2021/073303. Such methods of synthesis are here by incorporated in their entirety by reference.

Additional embodiments of the current invention include a compound of Formula I-XI, or a pharmaceutically acceptable salt, solvate, stereoisomer, tautomer, or prodrug thereof, for use in recreational, psychological, or medical therapies.

One embodiment of the present invention provides a systems, methods, and compositions for novel psilocin prodrugs according to the compounds of Formula I-XI (also referred to as a/the compound(s) of the invention) and a pharmaceutically acceptable carrier or diluent, which may preferably further include a method of treatment of the human or animal body using one or more of the novel compounds, or pharmaceutical compositions described herein.

In another embodiment, the present invention provides the use of one or more of the novel psilocin prodrugs according to the compounds of Formula I-XI are serotonin receptor agonists. As used herein, a "serotonin receptor agonists" means a substance, and preferably a compound of the invention, having the function of acting on a serotonin receptor, and includes, for example, a 5-HT2A, 5-HT2C and 5-HT1A 5-HT2A receptor agonist. As used herein, an "agonist" means a substance, and preferably a compound of the invention, having the function of binding/activating to a receptor or to produce a biological response. In another embodiment, the present invention provides the use of one or more of the novel psilocin prodrugs according to the compounds of Formula I-XI for the treatment of a disease or condition, and preferably a disease or condition in a subject that is may be treated by activating of one or more serotonin receptors by the agonist action of one or more compounds of the invention in a subject in need thereof.

A compound of Formula I-XI, or a pharmaceutically acceptable salt thereof, for use in the modulation of serotonin receptor activity in research, pharmaceutical, and biotechnology development. A compound of Formula I-XI, or a pharmaceutically acceptable salt thereof, for use in the treatment of a disease or condition in which modulation of serotonin receptor activity is beneficial.

A method for treating a disease or condition for which modulation of serotonin receptor activity is beneficial comprising the steps of administering to a subject in need thereof, a therapeutically effective amount of a compound of I—, or a pharmaceutically acceptable salt thereof. A method for treating a disease or condition for which modulation of serotonin receptor is beneficial comprising the steps of administering to a subject in need thereof, a therapeutically effective amount of a combination comprising a compound of Formula I-XI, or a pharmaceutically acceptable salt thereof, and at least one further therapeutic agent, wherein said further therapeutic agent may optionally be a serotonin receptor agonist, or a Monoamine Oxidase Inhibitors (MAOIs).

A method for treating a disease or condition for which modulation of serotonin receptor is beneficial comprising: administering to a subject in need thereof, a therapeutically effective amount of a combination comprising a compound of Formula I-XI, or a pharmaceutically acceptable salt thereof, and at least one further therapeutic agent, wherein said further therapeutic agent is selected from the group consisting of: 1) a tryptamine compound, or a tryptamine compound and an entactogen. As used herein, "tryptamine" means compounds having affinity for a serotonin receptor and may include, but not be limited to: substituted tryptamines, psilocybin, psilocin, N,N-dimethyltryptamine, 5-methoxy-N,N-dimethyltryptamine, N,N-Dipropyltryptamine, 5-methoxy-N,N-Dipropyltryptamine, baeocystin ([3-[2-(methylamino)ethy 1]-1H-indol-4-yl] di hydrogen phosphate), norbaeocystin ([3-(2-aminoethyl)-1H-indol-4-yl] dihydrogen phosphate), aeruguinascin (N,N,N-trimethyl-4-phosphorl-oxytryptamine), 4-acetoxy-N,N-dimethyltryptamine, 3-(2'-dimethylaminoethy 1)-4-acetoxy-indole. As used herein, "entactogens" means a compounds having the effect of releasing serotonin, norepinephrine and dopamine such as 3,4-methylenedioxyamphetamine (MDMA), 2,5-dimethoxy-4-bromophenethylamine, 3,4-methylenedioxyN-ethylamphetamine, a-lfamethyltryptamine and alpha-ethyltryptamine.

The use of a compound of Formula I-XI, or a pharmaceutically acceptable salt thereof, in the manufacture of a pharmaceutical composition for use the treatment of a disease or condition for which modulation of serotonin receptor is beneficial. A pharmaceutical composition comprising a compound of Formula I-XI, or a pharmaceutically acceptable salt thereof, for use in the treatment of a disease or condition for which modulation of serotonin receptor is beneficial. A pharmaceutical composition comprising a compound of Formula I-XI, or a pharmaceutically acceptable salt thereof, and at least one further therapeutic agent, wherein said further therapeutic agent is optionally selected from the group consisting of: 1) a tryptamine compound, and/or an entactogen for use in the treatment of a disease or condition for which modulation of serotonin receptor activity is beneficial.

A compound of the invention or pharmaceutical composition comprising the compound may be administered to a "subject," and preferably a human subject, by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly. The subject may be a eukaryote, an animal, a vertebrate animal, a mammal, a rodent (e.g., a guinea pig, a hamster, a rat, a mouse), murine (e.g., a mouse), canine (e.g., a dog), feline (e.g., a cat), equine (e.g., a horse), a primate, simian (e.g., a monkey or ape), a monkey (e.g., marmoset, baboon), an ape (e.g., gorilla, chimpanzee, orangutang, gibbon), or a human.

While it is possible for the active compound to be administered alone, it is preferable to present it as a pharmaceutical composition (e.g., formulation) comprising at least one active compound, as defined above, together with one or more pharmaceutically acceptable carriers, adjuvants, excipients, diluents, fillers, buffers, stabilizers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilizers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, diluents, excipients, etc. can be found in standard pharmaceutical texts. See, for example, "Handbook of Pharmaceutical Additives", 2nd Edition (eds. M. Ash and I. Ash), 2001 (Synapse Information Resources, Inc., Endicott, N.Y., USA), "Remington's Pharmaceutical Sciences", 20th edition, pub. Lippincott, Williams & Wilkins, 2000; and "Handbook of Pharmaceutical Excipients", 2nd edition, 1994.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary, shaping the product.

Formulations may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g., by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or molding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g., sodium lauryl sulfate); and preservatives (e.g., methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrants will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet. Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet. Other conventional ingredients include anti-oxidants, colorants, flavoring agents, preservatives and taste-masking agents. Exemplary tablets contain up to about 80 wt % drug, from about 10 wt % to about 90 wt % binder, from about O wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tableting. The final formulation may include one or more layers and may be coated or uncoated; or encapsulated. The formulation of tablets is discussed in detail in "Pharmaceutical Dosage Forms: Tablets, Vol. 1", by H. Lieberman and L. Lachman, Marcel Dekker, N.Y., N.Y., 1980 (ISBN 0-8247-6918-X), the disclosure of which is incorporated herein by reference in its entirety. Solid formulations for oral administration may be formulated to be immediate and/or modified release. Modified release formulations include delayed-, sustained-pulsed-, controlled-, targeted and programmed release. Suitable modified release formulations are described in U.S. Pat. No. 6,106,864.

Details of other suitable release technologies such as high energy dispersions and osmotic and coated particles can be found in Verma et al, Pharmaceutical Technology On-line, 25(2), 1-14 (2001). The use of chewing gum to achieve controlled release is described in WO 00/35298. The disclosures of these references are incorporated herein by reference in their entireties.

Formulations suitable for topical administration (e.g., transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents. Formulations suitable for topical administration in the mouth include lozenges comprising the active compound in a flavored basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the active compound.

Formulations suitable for administration by inhalation include those presented as an aerosol spray from a pressurized pack, with the use of a suitable propellant, such as dichlorodifluoromethane, trichlorofluoromethane, dichorotetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Suitable emulgents and emulsion stabilizers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams, or spray formulations containing in addition to the active compound, such carriers as are known in the art to be appropriate.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilizers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 μg to about 250 mg per kilogram body weight of the subject per day. Where the active compound is a salt, an ester, prodrug, or the like, the amount administered is calculated on the basis of the parent compound and so the actual weight to be used is increased proportionately.

The invention now being generally described will be more readily understood by reference to the following examples, which are included merely for the purposes of illustration of certain embodiments of the embodiments of the present invention. The examples are not intended to limit the invention, as one of skill in the art would recognize from the above teachings and the following examples that other techniques and methods can satisfy the claims and can be employed without departing from the scope of the claimed invention. Indeed, while this invention has been particularly shown and described with references to preferred embodiments thereof, it will be understood by those skilled in the art that various changes in form and details may be made therein without departing from the scope of the invention encompassed by the appended claims.

EXAMPLES

Example 1: Synthesis of 3-(2-(dimethylamino)ethyl)-1H-indol-4-yl ethyl carbonate As shown in Scheme 1 below, the present invention provides for the step wise production of novel psilocin prodrug analog 3-(2-(dimethylamino)ethyl)-1H-indol-4-yl ethyl carbonate also referred to herein as MY276 and Formula VI:

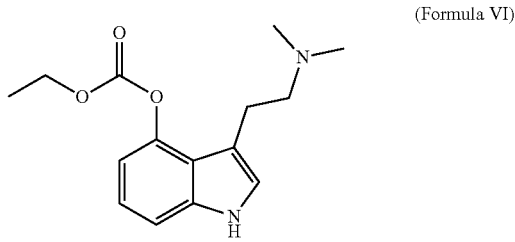

(Formula VI)

according to the following scheme:

Scheme 1

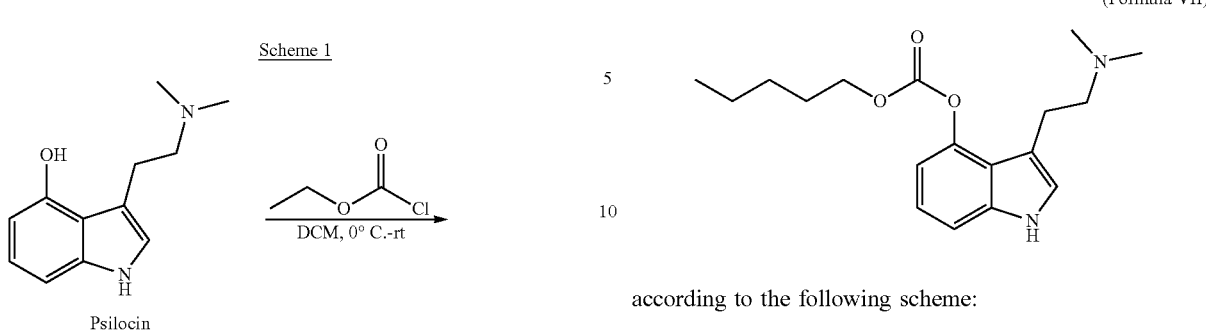

As described in Scheme 1 above, in this embodiment, the present inventors demonstrated the synthesis of the novel psilocin prodrug analog compound MY276. To a clear solution of Psilocin (0.20 g, 0.96 mmol, 1 eq) in anhydrous DCM (15 mL) at 0-5° C. under nitrogen was added triethylamine (0.27 mL, 1.92 mmol, 2.0 eq) and ethyl chloroformate (0.13 g, 1.15 mmol, 1.2 eq) slowly via a syringe. The resultant mixture was stirred for 16 h at 5° C. The reaction mixture was analyzed by TLC to check the progress of the reaction and confirm the completion of the reaction. The reaction mixture was quenched with water (10 mL) and saturated NaHCO$_3$ aqueous solution (10 mL), and the layers were separated (organic and aqueous). The DCM layer was dried over Na$_2$SO$_4$, concentrated under vacuum to get the crude product (oil). The crude oil was purified by silica gel chromatography eluted with NH4OH/MeOH/DCM (0.01/1/20) to get 3-(2-(dimethylamino)ethyl)-1H-indol-4-yl ethyl carbonate as off-white solid (0.042 g, yield 16%, Lot #: MNC-4R-9). $^1$H NMR (600 MHz, CDCl$_3$): δ 8.13 (br s, 1H), 7.25 (d, J=7.8 Hz, 1H), 7.15 (d, J=7.8 Hz, 1H), 7.01 (s, 1H), 6.92 (d, J=7.8 Hz, 1H), 4.38 (q, J=7.2 Hz, 2H), 2.97 (m, 2H), 2.65 (m, 2H), 2.36 (s, 6H), 1.42 (t, J=7.2 Hz, 3H). $^{13}$C NMR (150 MHz, CDCl$_3$): δ 154.1, 144.7, 138.6, 122.4, 122.1, 119.8, 113.3, 111.8, 109.3, 64.7, 60.9, 45.4, 24.5, 14.3.

LCMS (ES) m/z calc. for C$_{15}$H$_{21}$N$_2$O$_3$ (M+1)+, 277.2; found, 277.2

Example 2: Synthesis of 3-(2-(dimethylamino)ethyl)-1H-indol-4-yl pentyl carbonate As shown in Scheme 2 below, the present invention provides for the step wise production of novel psilocin prodrug analog 3-(2-(dimethylamino)ethyl)-1H-indol-4-yl pentyl carbonate also referred to herein as MY318 and Formula VII:

(Formula VII)

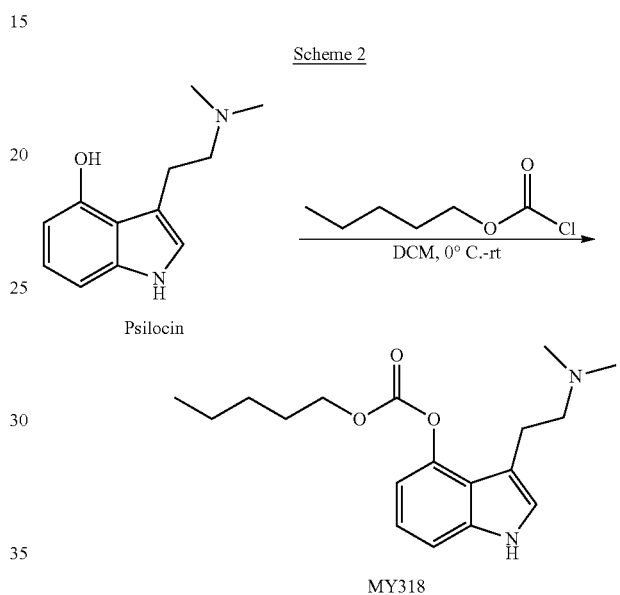

according to the following scheme:

Scheme 2

As described in Scheme 2 above, in this embodiment, the present inventors demonstrated the synthesis of the novel psilocin prodrug analog compound MY318. To a clear solution of Psilocin (0.10 g, 0.48 mmol, 1 eq) in anhydrous DCM (10 mL) at 0-5° C. under nitrogen was added triethylamine (0.13 mL, 0.96 mmol, 2.0 eq) and ethyl chloroformate (0.08 g, 0.59 mmol, 1.2 eq) slowly via a syringe. The resultant mixture was stirred for 16 h at 5° C. The reaction mixture was analyzed by TLC to check the progress of the reaction and confirm the completion of the reaction. The reaction mixture was quenched with water (10 mL) and saturated NaHCO$_3$ aqueous solution (10 mL), and the layers were separated (organic and aqueous). The DCM layer was dried over Na$_2$SO$_4$, concentrated under vacuum to get the crude product (oil). The crude oil was purified by silica gel chromatography eluted with NH4OH/MeOH/DCM (0.01/1/20) to get 3-(2-(dimethylamino)ethyl)-1H-indol-4-yl pentyl carbonate as off-white solid (0.068 g, yield 45%, Lot #: MNC-4R-8). $^1$H NMR (600 MHz, CDCl$_3$): δ 8.16 (br s, 1H), 7.24 (d, J=7.8 Hz, 1H), 7.16 (d, J=7.8 Hz, 1H), 7.01 (s, 1H), 6.93 (d, J=7.8 Hz, 1H), 4.30 (t, J=7.2 Hz, 2H), 2.98 (m, 2H), 2.66 (m, 2H), 2.35 (s, 6H), 1.78 (m, 2H), 1.42 (m, 4H), 0.98 (t, J=7.2 Hz, 3H). $^{13}$C NMR (150 MHz, CDCl$_3$): δ 154.2, 144.7, 138.6, 122.4, 122.0, 119.8, 113.2, 111.8, 109.3, 68.9, 60.8, 45.3, 28.3, 27.8, 24.5, 22.3, 13.9. LCMS (ES) m/z calc. for C$_{18}$H$_{27}$N$_2$O$_3$ (M+1)+, 319.2; found, 319.2

Example 3: Synthesis of -(2-(Dimethylamino)ethyl)-1H-indol-4-yl hexylcarbamate As shown in Scheme 3 below, the present invention provides for the step wise production of novel psilocin prodrug analog -(2-(Dimethylamino)ethyl)-1H-indol-4-yl hexylcarbamate also referred to herein as MY331 and Formula VIII:

(Formula VIII)

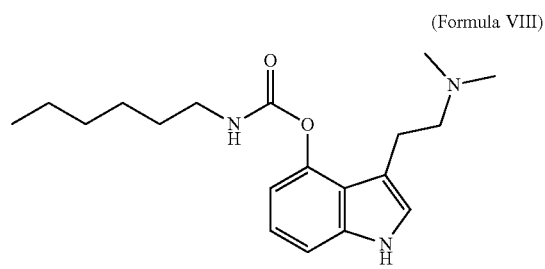 [SMILES: CCCCCCNC(=O)Oc1cccc2[nH]cc(CCN(C)C)c12]

according to the following scheme:

Scheme 3

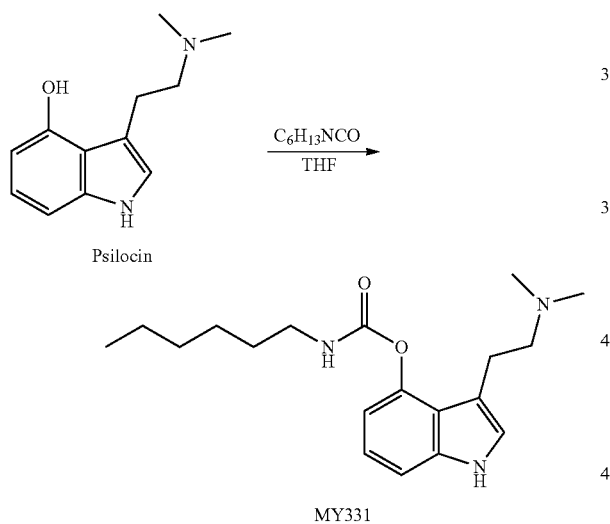

As described in Scheme 3 above, in this embodiment, the present inventors demonstrated the synthesis of the novel psilocin prodrug analog compound MY331. To a clear solution of Psilocin (0.30 g, 1.47 mmol, 1 eq) in anhydrous tetrahydrofuran (15 mL) at room temperature under nitrogen was added hexyl isocyanate (0.34 g, 2.67 mmol, 1.8 eq) slowly via a syringe. The resultant mixture was stirred and heated to 50° C. for 16 h. TLC indicated that the reaction was near finished (desired product Rf 0.15; starting material Psilocin Rf 0.2; Silica plate, 0.5% concentrated NH₄OH aq/5% MeOH in DCM). The reaction mixture was concentrated under vacuum. The residue was purified by silica gel chromatography eluting with 2%~4% (10% NH4OH aq/MeOH) in DCM to afford the desired product -(2-(Dimethylamino)ethyl)-1H-indol-4-yl hexylcarbamate (MY331) as colorless gum (0.24 g, yield 49%). 1H NMR (600 MHz, CDCl₃): δ 8.05 (br s, 1H), 7.03-7.08 (m, 2H), 6.94 (dd, J=1.2 and 7.2 Hz, 1H), 6.82 (d, J=1.8 Hz, 1H), 6.27 (br s, 1H), 3.18-3.19 (m, 2H), 2.86 (dt, J=1.8 and 7.8 Hz, 2H), 2.54 (t, J=7.8 Hz, 2H), 2.23 (s, 6H), 1.29 -1.30 (m, 2H), 1.24-1.26 (m, 6H), 0.83 (t, J=7.2 Hz, 3H). ¹³C NMR (150 MHz, CDCl₃): d 155.1, 144.8, 138.5, 122.3, 121.7, 120.1, 113.5, 112.3, 106.4, 61.2, 45.5, 41.2, 31.5, 29.8, 26.5, 26.1, 22.5. LCMS m/z=332 [M+1]⁺

Example 4: Synthesis of 3-(2-(dimethylamino)ethyl)-1H-indol-4-yl hexyl carbonate As shown in Scheme 4 below, the present invention provides for the step wise production of novel psilocin prodrug analog 3-(2-(dimethylamino)ethyl)-1H-indol-4-yl hexyl carbonate also referred to herein as MY332 and Formula IX:

(Formula IX)

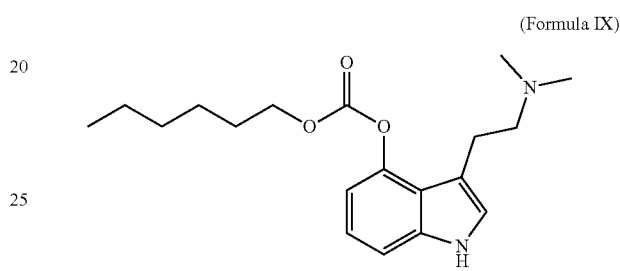

according to the following scheme:

Scheme 4

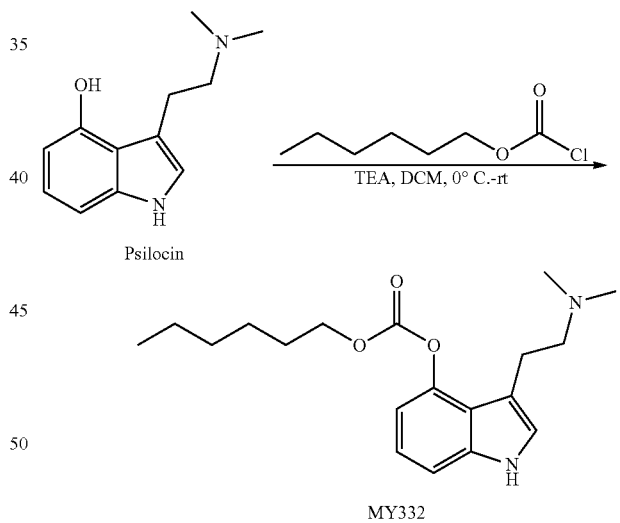

As described in Scheme 4 above, in this embodiment, the present inventors demonstrated the synthesis of the novel psilocin prodrug analog compound MY332. To a clear solution of Psilocin (0.50 g, 2.44 mmol, 1 eq) in anhydrous DCM (40 mL) at 0-5° C. under nitrogen was added triethylamine (0.68 mL, 4.88 mmol, 2.0 eq) and hexyl chloroformate (0.49 g, 2.94 mmol, 1.2 eq) slowly via a syringe. The resultant mixture was stirred for 3 h at 20° C. The reaction mixture was analyzed by TLC to check the progress of the reaction and confirm the completion of the reaction. The reaction mixture was quenched with water (10 mL) and saturated NaHCO₃ aqueous solution (10 mL), and the layers were separated (organic and aqueous). The DCM layer was dried over Na$_2$SO$_4$, concentrated under vacuum to get the crude product (oil). The crude oil was purified by silica gel chromatography eluted with NH4OH/MeOH/DCM (0.01/1/20) to give MY332 and Psilocin (4:1). The MY332 was unstable under chromatography condition. The residue was washed with (3:1) Hexane:EtOAc to provide 3-(2-(dimethylamino)ethyl)-1H-indol-4-yl hexyl carbonate as off-white solid (0.085 g, yield 10%, Lot #: MNC-4R-78-3). $^1$H NMR (600 MHz, CDCl$_3$): δ 8.21 (br s, 1H), 7.23 (d, J=7.8 Hz, 1H), 7.15 (t, J=7.8 Hz, 1H), 7.01 (s, 1H), 6.92 (d, J=7.8 Hz, 1H), 4.30 (t, J=7.2 Hz, 2H), 2.97 (m, 2H), 2.65 (m, 2H), 2.35 (s, 6H), 1.78 (m, 2H), 1.46 (m, 2H), 1.34 (m, 4H), 0.94 (t, J=7.2 Hz, 3H). $^{13}$C NMR (150 MHz, CDCl$_3$): d 154.3, 144.7, 138.6, 122.5, 122.0, 119.8, 113.3, 111.8, 109.3, 68.9, 60.9, 45.4, 31.4, 28.6, 25.4, 24.5, 22.5, 14.0. LCMS (ES) m/z calc. for C$_{19}$H$_{29}$N$_2$O$_3$ (M+1)+, 333.2; found, 333.3.

Example 5: Synthesis of MY333A

As shown in Scheme 5 below, the present invention provides for the step wise production of novel psilocin prodrug analog referred to herein as MY333A and Formula X:

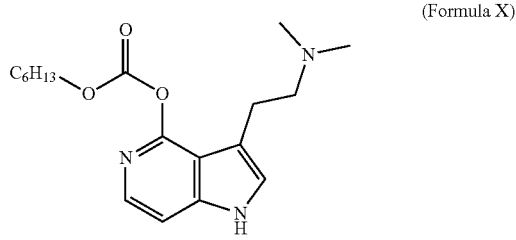
(Formula X)

according to the following scheme:

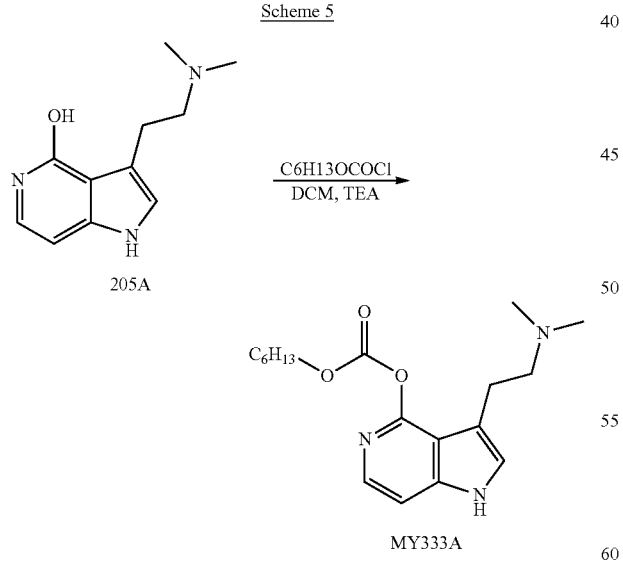

As described in Scheme 5 above, in this embodiment, the present inventors demonstrated the synthesis of the novel psilocin prodrug analog compound MY333A. To a clear solution of 205A (0.040 g, 0.20 mmol, 1 eq) in anhydrous DCM (10 mL) at (0 to 5) ° C. under nitrogen were added C6H13OCOCl (0.032 g, 0.20 mmol, 1.0 eq) and trimethylamine (0.056 mL, 0.40 mmol, 2 eq) slowly via a syringe. The resultant mixture is allowed to warm to rt and concentrated under vacuum to get the crude product (oil), which was purified by chromatography (silica gel, DCM/MeOH/NH4OH=5/1/0.1) to provide compound MY333A (4.2 mg, Lot #: MNC-4R-109) as white solid. $^1$H NMR (600 MHz, CDCl$_3$): d 10.5 (br s, 1H), 7.24 (s, 1H), 7.16 (d, J=7.2 Hz, 1H), 7.09 (d, J=7.2 Hz, 1H), 4.30 (t, J=6.6 Hz, 2H), 3.16 (m, 2H), 3.05 (m, 2H), 2.58 (s, 6H), 1.74 (m, 2H), 1.40 (m, 2H), 1.29 (m, 4H), 0.84 (m, 3H). LCMS (ES) m/z calc. for C$_{18}$H$_{28}$N$_3$O$_3$ (M+1)+, 334.2; found, 334.2.

Example 6: Synthesis of MY333B

As shown in Scheme 6 below, the present invention provides for the step wise production of novel psilocin prodrug analog referred to herein as MY333B and Formula XI:

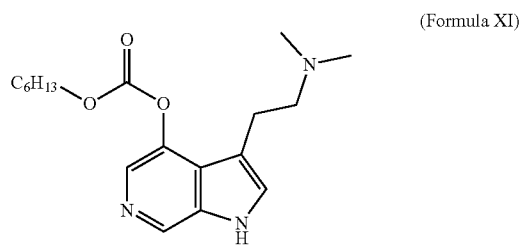
(Formula XI)

according to the following scheme:

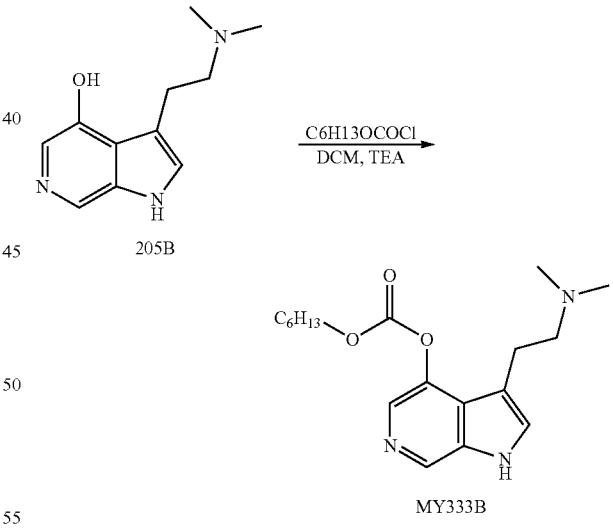

As described in Scheme 6 above, in this embodiment, the present inventors demonstrated the synthesis of the novel psilocin prodrug analog compound MY333B. To a clear solution of 205B (0.060 g, 0.29 mmol, 1 eq) in anhydrous DCM (35 mL) at (0 to 5) ° C. under nitrogen were added C6H13OCOCl (0.057 g, 0.35 mmol, 1.2 eq) and trimethylamine (0.080 mL, 0.58 mmol, 2 eq) slowly via a syringe. The resultant mixture is allowed to warm to rt and concentrated under vacuum to get the crude product, which was purified by chromatography (silica gel, DCM/MeOH=10/1) to provide compound MY333B (13.9 mg, Lot #: MNC-4R-

107) as beige oil. $^1$H NMR (600 MHz, CDCl$_3$): δ 8.86 (s, 1H), 7.98 (s, 1H), 7.35 (s, 1H), 4.37 (t, J=6.6 Hz, 2H), 2.87 (m, 2H), 2.70 (m, 2H), 2.36 (s, 6H), 1.78 (m, 2H), 1.40 (m, 2H), 1.27 (m, 4H), 0.84 (m, 3H). LCMS (ES) m/z calc. for C$_{18}$H28N$_3$O$_3$ (M+1)+, 334.2; found, 334.2.

Example 7: Synthesis of Psilocin Prodrug Analog 3-(2-(dimethylamino)ethyl)-1H-pyrrolo[3,2-c]pyridin-4-ol In one embodiment, the invention include methods of synthesizing the psilocin prodrug intermediate MY205A or 205A, which as noted above can form starting compound for MY333A, MY205A having the following structure:

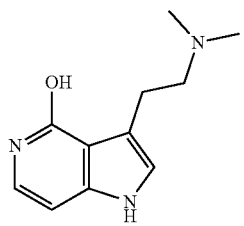

MY205A according to the following scheme:

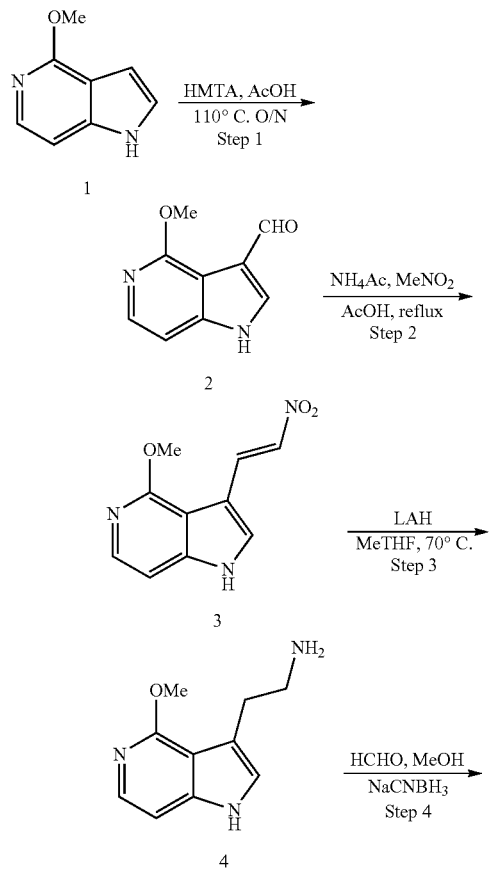

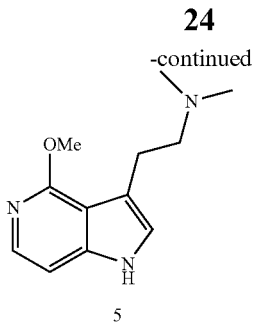

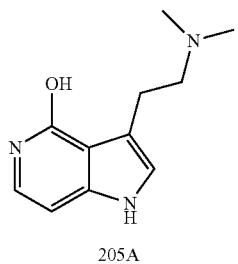

Synthesis of Novel Psilocin Prodrug Analog intermediate 4-methoxy-1H-pyrrolo[3,2-c]pyridine-3-carbaldehyde (2)

As described in Scheme 7 above, in this embodiment, the present inventors demonstrated the synthesis of the psilocin prodrug analog intermediate compound 2. In this embodiment, to a stirred suspension of 4-methoxy-1H-pyrrolo[3,2-c]pyridine 1 (2.6 g, 17.0 mmol, 1.0 eq) in acetic acid (15 mL) and water (15 mL) was added hexamethylenetetramine (2.5 g, 17.0 mmol, 1.0 eq). The resultant mixture was stirred and heated at 90° C. for 15 hours. TLC indicated the reaction was completed. The reaction mixture was neutralized with NaOH to pH=7, extracted with 10% MeOH in EtOAc and concentrated under vacuum to afford the residue, which was purified by chromatography (silica gel, 10% MeOH in DCM) to provide compound 2 (0.72 g, 24% yield, Lot #: MNC-4R-94) as yellow solid. $^1$H NMR (600 MHz, CDCl$_3$): δ 12.51 (br s, 1H), 10.26 (s, 1H), 8.14 (s, 1H), 7.80 (d, J=6.0 Hz, 1H), 7.16 (d, J=6.0 Hz, 1H), 4.06 (s, 3H).

Synthesis of 4-methoxy-3-(2-nitrovinyl)-1H-pyrrolo[3,2-c]pyridine (3)

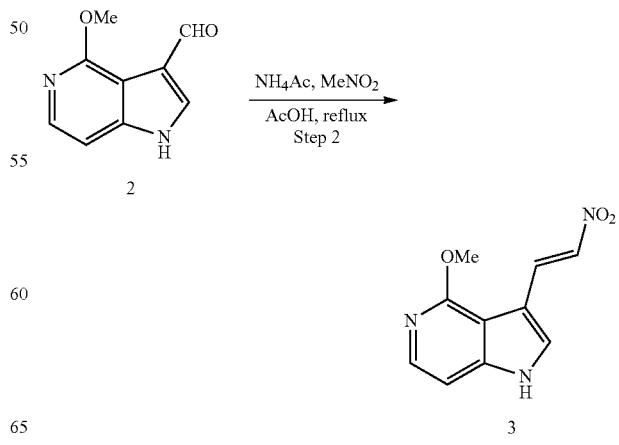

As described in Scheme 6 above, in this embodiment, the present inventors demonstrated the synthesis of the psilocin prodrug analog intermediate compound 3. In this embodiment, to a suspension of 2 (0.72 g, 4.1 mmol, 1.0 eq) in acetic acid (4.5 mL) was added nitromethane (1.4 mL, 28.7 mmol, 7.0 eq) followed by ammonium acetate (0.38 g, 4.9 mmol, 1.2 eq). The resultant mixture was stirred and heated at 100° C. for 1.5 h and TLC indicated that the reaction was completed. The reaction mixture was cooled to room temperature, quenched with water, stirred for 2h, filtered and died to provide compound 3 (0.60 g, 67% yield, Lot #: MNC-4R-95) as yellow solid. $^1$H NMR (600 MHz, DMSO-$d_6$): δ 12.47 (br s, 1H), 8.45 (d, J=13.2 Hz, 1H), 8.28 (s, 1H), 8.21 (d, J=13.2 Hz, 1H), 7.89 (d, J=6.0 Hz, 1H), 7.15 (d, J=6.0 Hz, 1H), 4.06 (s, 3H).

Synthesis of 2-(4-methoxy-1H-pyrrolo[3,2-c]pyridin-3-yl)-N,N-dimethylethanamine (5)

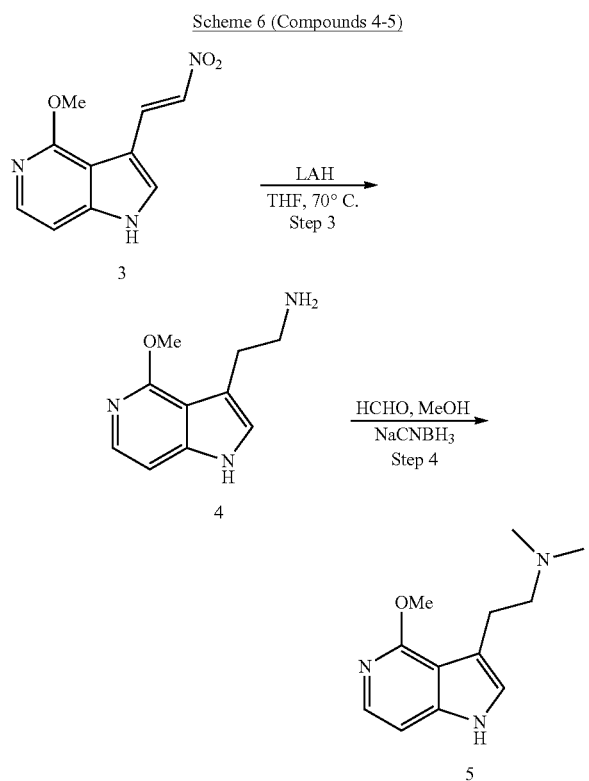

As described in Scheme 6 above, in this embodiment, the present inventors demonstrated the synthesis of the psilocin prodrug analog intermediate compounds 4-5. In this embodiment, to a stirred solution of compound 3 (0.60 g, 2.74 mmol, 1.0 eq) in THF (anhydrous, 200 mL) under nitrogen at 0° C. to 5° C. was added LAH (1M in THF, 16.5 mL, 16.4 mmol, 6.0 eq) slowly via a syringe. The resulting yellow suspension was stirred at 70° C. for 16 hours. After cooling to 0° C. to 5° C., the reaction was quenched with water and NaOH, filtered and concentrated to provide colorless oil (0.54 g). To this oil in MeOH (30 mL) was added HCHO (4.5 mL), HOAc (0.63 mL) and NaCNBH3 (0.86 g) in portions. The mixture was stirred at rt for 1.5 h and concentrated to provide the residue, which was purified by chromatography (silica gel, DCM/MeOH/NH4OH=8/1/0.1) to provide compound 5 (0.47 g, 78% yield, Lot #: MNC-4R-103) as a colorless oil. $^1$H NMR (600 MHz, CDCl$_3$): δ 8.29 (s, 1H), 7.71 (d, J=6.0 Hz, 1H), 6.81 (s, 1H), 6.79 (d, J=6.0 Hz, 1H), 4.00 (s, 1H), 2.99 (m, 2H), 2.58 (m, 2H), 2.29 (s, 6H).

Synthesis of 3-(2-(dimethylamino)ethyl)-1H-pyrrolo[3,2-c]pyridin-4-ol (205A)

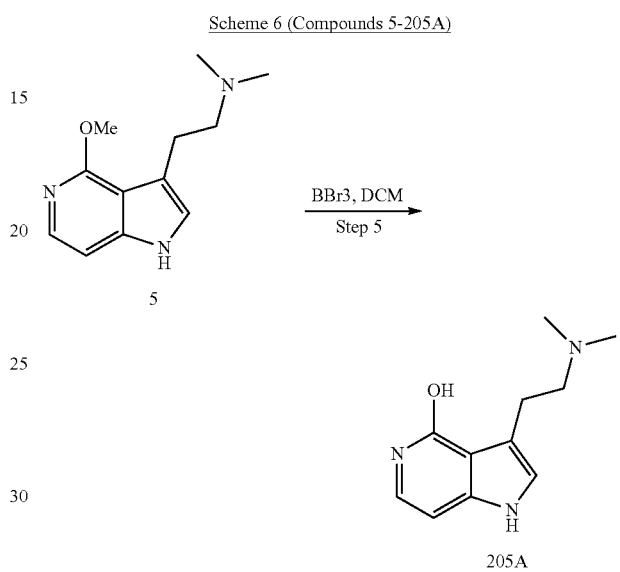

As described in Scheme 6 above, in this embodiment, the present inventors demonstrated the synthesis of the psilocin prodrug analog compound 205A (also described herein as MY205A). In this embodiment, to a solution of 5 (0.11 g, 0.50 mmol) in dichloroethane (4 mL) under nitrogen was added boron tribromide (0.4 mL) slowly via a syringe. The resultant suspension was stirred at 0° C. to room temperature for 24 hours. After cooling to 0° C. to 5° C., the reaction mixture was quenched by adding MeOH and concentrated under vacuum to give a residue, which was purified by chromatography (silica gel, DCM/MeOH/NH4OH=5/1/0.1) to provide compound MY205A (0.065 g, 63% yield, Lot #: MNC-4R-102-1) as off-white solid. $^1$H NMR (600 MHz, CH3OD): d 7.02 (d, J=7.2 Hz, 1H), 6.96 (s, 1H), 6.52 (d, J=7.2 Hz, 1H), 3.34 (t, J=7.2 Hz, 2H), 3.13 (t, J=7.2 Hz, 2H), 2.82 (s, 6H). $^{13}$C NMR (150 MHz, DMSO-$d_6$): δ 160.96, 140.25, 127.91, 121.23, 115.26, 113.33, 96.21, 58.63, 42.93, 21.51. LCMS (ES) m/z calc. for $C_{11}H_{16}N_3O$ (M+1)+, 206.1; found, 206.0

Definitions

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a 13C- or 14C-enriched carbon are within the scope of this invention. Such compounds are useful, for example, as analytical tools, as probes in biological assays, or as therapeutic agents in accordance with the present invention. The term "stereoisomer" refers to a molecule that is an enantiomer, diastereomer or geometric isomer of a molecule. Stereoisomers, unlike structural isomers, do not differ with respect to the number and types of atoms in the molecule's structure but with respect to the spatial arrangement of the molecule's atoms. Examples of stereoisomers include the (+) and (−) forms of optically active molecules.

As used herein the singular forms "a", "an", and "the" include plural referents unless the context clearly dictates otherwise. Thus, for example, reference to "a compound" includes a plurality of such compounds, and reference to "the method" includes reference to one or more methods, method steps, and equivalents thereof known to those skilled in the art, and so forth. Similarly, the word "or" is intended to include "and" unless the context clearly indicates otherwise. Hence "comprising A or B" means including A, or B, or A and B. Furthermore, the use of the term "including", as well as other related forms, such as "includes" and "included", is not limiting.

The term "about" as used herein is a flexible word with a meaning similar to "approximately" or "nearly". The term "about" indicates that exactitude is not claimed, but rather a contemplated variation. Thus, as used herein, the term "about" means within 1 or 2 standard deviations from the specifically recited value, or ± a range of up to 20%, up to 15%, up to 10%, up to 5%, or up to 4%, 3%, 2%, or 1% compared to the specifically recited value.

The term "compound," "active compound," or "composition," or "compound of the invention" includes all solvates, complexes, polymorphs, radiolabeled derivatives, tautomers, stereoisomers, and optical isomers of the novel psilocin prodrug compounds generally described herein, and salts thereof, unless otherwise specified. Notably, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: acetic, propionic, succinic, gycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetoxybenzoic, fumaric, toluenesulfonic, methanesulfonic, ethanesulfonic, ethane disulfonic, oxalic, isethionic, valeric, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc. It may be convenient or desirable to prepare, purify, and/or handle the active compound in a chemically protected form. The term "chemically protected form," as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, "Protective Groups in Organic Synthesis" (T. Green and P. Wuts; 3rd Edition; John Wiley and Sons, 1999). For example, a hydroxy group may be protected as an ether (—OR) or an ester (—OC(═O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(═O)CH$_3$, OAc).

For example, an aldehyde or ketone group may be protected as an acetal or ketal, respectively, in which the carbonyl group (>C═O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide or a urethane, for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C6H$_5$, —NH-Bpoc), as a 9-fluorenylmethoxy amide (—NH-Fmoc), as a 6-nitroveratryloxy amide (—NH—Nvoc), as a 2-trimethylsilylethyloxy amide (—NH— Teoc), as a 2,2,2-trichloroethyloxy amide (—NH-Troc), as an allyloxy amide (—NH-Alloc), as a 2(-phenylsulphonyl)ethyloxy amide (—NH— Psec); or, in suitable cases, as an N-oxide (>NO). For example, a carboxylic acid group may be protected as an ester for example, as: a C$_{1-7}$ alkyl ester (e.g., a methyl ester; a t-butyl ester); a C$_{1-7}$ haloalkyl ester (e.g., a C$_{1-7}$ trihaloalkyl ester); a triC$_{1-7}$ alkylsilyl-C$_{1-7}$ alkyl ester; or a C$_{5-20}$ aryl-C$_{1-7}$ alkyl ester (e.g., a benzyl ester; a nitrobenzyl ester); or as an amide, for example, as a methyl amide. In a preferred embodiment an amine, such as (CH3)2NH (dimethylamine), or CH3CH(CH3)NHCH(CH3)CH3 (diisopropylamine) may be coupled with a an linear alkane, such as CH2CH2.

For example, a thiol group may be protected as a thioether (—SR), for example, as: a benzyl thioether; an acetamidomethyl ether (—S—CH$_2$NHC(═O)CH$_3$).

"Carbonate" as used here means a substituent, moiety or group that contains a —O—C(═O)—O-structure (i.e., carbonate functional group). Typically, carbonate groups as used here comprise or consist of an organic moiety, wherein the organic moiety is as described herein for an organic moiety bonded to an ester functional group, bonded through the —O—C(═O)— structure, e.g., organic moiety —O—C(═O)—O—. When carbonate is used as a Markush group (i.e., a substituent) one of the singly bonded oxygen atoms of the carbonate functional group is attached to a Markush formula with which it is associated and the other is bonded to a carbon atom of an organic moiety as previously described for an organic moiety bonded to an ester functional group.

"Carbamate" as used here means a substituent, moiety or group that contains a structure represented by O—C(═O)N(R$^a$) (i.e., carbamate functional group) or —C(═O)N(R$^a$)$_2$, —O—C(═O)NH (optionally substituted alkyl) or —O—C(═O)N (optionally substituted alkyl)$_2$ (i.e., exemplary carbamate substituents) wherein R$^a$ and optionally substituted alkyl are independently selected wherein R$^a$, independently selected, is hydrogen, a protecting group or an organic moiety, wherein the organic moiety is as described herein for an organic moiety bonded to an ester functional group and is typically an optionally substituted alkyl. Typically, carbamate groups as used herein comprise or consist of an organic moiety, independently selected from R$^a$, wherein the organic moiety is as described herein for an organic moiety bonded to an ester functional group, bonded through the —O—C(═O)—N(R)— structure, wherein the resulting structure has the formula of organic moiety —O—C(═O)—N(R)— or —O—C(═O)—N(R$^a$)— organic moiety. When carbamate is used as a Markush group (i.e., a substituent), the singly bonded oxygen (O-linked) or nitrogen (N-linked) of the carbamate functional group is attached to a Markush formula with which it is associated. The linkage of the carbamate substituent is either explicitly stated (N- or O-linked) or implicit in the context to which this substituent is referred.

As used herein, "carboxyesterases" are defined as enzymes that naturally have catalytic activity toward the hydrolysis of carboxyesters which results in the formation of an organic acid and an alcohol.

As used herein, the term "alcohol" means an alcohol that comprises a C1-12 alkyl moiety substituted at a hydrogen atom with one hydroxyl group. Alcohols include methanol, ethanol, n-propanol, n-butanol, n-pentanol, n-hexanol, n-heptanol, n-octanol, n-nonanol, n-decanol, n-undecananol, n-dodecananol, n-tridecananol, n-tertadecananol, n-pentadecanol, n-hexadecananol, n-heltadecananol, and n-octadecanol. The carbon atoms in alcohols can be straight, branched or cyclic. Alcohol includes any subset of the foregoing, for example C1-18 alcohols (alcohols having 1-18 carbon atoms). Additional embodiment include C1-x alcohols, where x is greater than 18. (alcohols having greater than 18 carbon atoms)

In the context of the present invention, C1-C18-alkyl represents a linear or branched C1-C18-alkyl radical, for example methyl, -ethyl, n-proply, n-butyl, n-pentyl, n-hexyl, n-heptyl, n-octyl, n-nonyl, n-decyl, n-undecanyl, n-dodecanyl, n-tridecanyl, n-tertadecanyl, n-pentadecanyl, n-hexadecanyl, n-heltadecanyl, and n-octadecanyl.

It may be convenient or desirable to prepare, purify, and/or handle the active compound in the form of a prodrug.

The term "prodrug", as used herein, pertains to a compound which, when metabolised (e.g., in vivo), yields the desired active compound. Typically, the prodrug is inactive, or less active than the active compound, but may provide advantageous handling, administration, or metabolic properties.

For example, some prodrugs are esters of the active compound (e.g., a physiologically acceptable metabolically labile ester). During metabolism, the ester group (—C(═O)OR) is cleaved to yield the active drug. Such esters may be formed by esterification, for example, of any of the carboxylic acid groups (—C(═O)OH) in the parent compound, with, where appropriate, prior protection of any other reactive groups present in the parent compound, followed by deprotection if required. Examples of such metabolically labile esters include, but are not limited to, those wherein R is C$_{1-20}$ alkyl (e.g. -Me, -Et); C$_{1-7}$ aminoalkyl (e.g. aminoethyl; 2-(N,N-diethylamino)ethyl; 2-(4-morpholino)ethyl); and acyloxy-C$_{1-7}$ alkyl (e.g. acyloxymethyl; acyloxyethyl; e.g. pivaloyloxymethyl; acetoxymethyl; 1-acetoxyethyl; 1-(1-methoxy-1-methyl)ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxy)carbonyloxyethyl; (4-tetrahydropyranyl) carbonyloxymethyl; and 1-(4-tetrahydropyranyl) carbonyloxyethyl).

Further suitable prodrug forms include phosphonate and glycolate salts. In particular, hydroxy groups (—OH), can be made into phosphonate prodrugs by reaction with chlorodibenzylphosphite, followed by hydrogenation, to form a phosphonate group —O—P(═O)(OH)$_2$. Such a group can be cleaved by phosphatase enzymes during metabolism to yield the active drug with the hydroxy group. Further "prodrugs" include carbamates and carbonates as described herein.

Also, some prodrugs are activated enzymatically to yield the active compound, or a compound which, upon further chemical reaction, yields the active compound. For example, the prodrug may be a sugar derivative or other glycoside conjugate or may be an amino acid ester derivative.

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen or nitrogen atom in the structures herein indicates the presence of a hydrogen atom. For convenience, the IUPAC numbering of the positions of representative pyrrolopyridinyl compounds described herein are shown by the formula

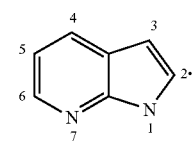

The positional numbering of pyrrolopyridinyl compounds remains the same for compounds in which the aza substitution shown at the 7-position in the above formula is moved to the 4-, 5- or 6-position of the above formula. Whenever a chiral carbon is present in a chemical structure, it is intended that all stereoisomers associated with that chiral carbon are encompassed by the structure.

An "R-group" or "substituent" refers to a single atom (for example, a halogen atom) or a group of two or more atoms that are covalently bonded to each other, which are covalently bonded to an atom or atoms in a molecule to satisfy the valency requirements of the atom or atoms of the molecule, typically in place of a hydrogen atom. Examples of R-group s/substituents include alkyl groups, hydroxyl groups, alkoxy groups, acyloxy groups, mercapto groups, and aryl groups.

The term "acyl" as used herein refers to a group of the formula C(=O)-D, where the acyl may be O-linked, and where D represents an alkyl, alkenyl, alkynyl, cycloalkyl, aryl, heteroaryl, cycloalkyl, or heterocycle, among others. Also, as used herein an "O-lined" acyl may also be referred to as an "O-linked ester". Typical examples are groups wherein D is a C1-C10 alkyl, C2-C10 alkenyl or alkynyl, or phenyl, each of which is optionally substituted. In some embodiments, D can be H, Me, Et, isopropyl, propyl, butyl, C1-C4 alkyl substituted with —OH, —OMe, or NH$_2$, phenyl, halophenyl, alkylphenyl, and the like. As noted above, an acyl may be an N- or O-linked acyl. Additional examples are groups wherein D is a H, $C_{1-12}$ alkyl (e.g., $C_{1-8}$, $C_{1-6}$, $C_{1-4}$, $C_{2-7}$, $C_{3-12}$, or $C_{3-6}$ alkyl), $C_{2-12}$ alkenyl (e.g., $C_{2-8}$, $C_{2-6}$, $C_{2-4}$, $C_{3-12}$, or $C_{3-6}$ alkenyl), $C_{6-20}$ aryl (e.g., $C_{6-15}$, $C_{6-10}$, $C_{8-20}$, or $C_{8-15}$ aryl), monocyclic $C_{1-6}$ heteroaryl (e.g., monocyclic $C_{1-4}$ or $C_{2-6}$ heteroaryl), $C_{4-19}$ heteroaryl (e.g., $C_{4-10}$ heteroaryl), $(C_{6-15})$aryl$(C_{1-6})$alkyl, $(C_{1-6})$heteroaryl$(C_{1-6})$alkyl, or $(C_{4-19})$heteroaryl$(C_{1-6})$alkyl. As used herein, "unsaturated" means that the compound has at least one degree of unsaturation (eg, at least one multiple bond) and includes partially and fully unsaturated compounds. As used herein, "saturated" means that the compound has no degree of unsaturation (eg, at least one multiple bond) and unless stated otherwise "saturated" means "fully saturated."

The term "acyloxy," as used herein means a group-OR, where R is each independently selected from substituted alkenyl, alkynyl, aryl, aralkyl, heteroaryl, aralkyl and acyl.

The term "alkyl" as used herein refers to saturated hydrocarbon groups in a straight, branched, or cyclic configuration or any combination thereof, and particularly contemplated alkyl groups include those having ten or less carbon atoms, especially 1-6 carbon atoms and lower alkyl groups having 1-4 carbon atoms. Exemplary alkyl groups are methyl, ethyl, propyl, isopropyl, butyl, sec-butyl, tertiary butyl, pentyl, isopentyl, hexyl, cyclopropylmethyl, etc. In one preferred embodiment, an "alkyl" refers to a branched or unbranched saturated hydrocarbon group of 1 to 24 carbon atoms, such as branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A"lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or (Ci-C$_6$)alkyl can be methyl, ethyl, propyl, isopropyl, butyl, iso-butyl, sec-butyl, pentyl, 3-pentyl, or hexyl; (C3-C6)cycloalkyl can be cyclopropyl, cyclobutyl, cyclopentyl, or cyclohexyl; (C$_3$-C$_6$)cycloalkyl(C$_1$-C$_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; (Ci-C$_6$)alkoxy can be methoxy, ethoxy, propoxy, isopropoxy, butoxy, iso-butoxy, sec-butoxy, pentoxy, 3-pentoxy, or hexyloxy; (C2-C$_6$)alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; (C$_2$-C$_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; (Ci-C$_6$)alkanoyl can be acetyl, propanoyl or butanoyl; halo(Ci-C$_6$)alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy(Ci-C$_6$)alkyl can be hydroxymethyl, 1-hydroxy ethyl, 2-hydroxy ethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; (Ci-C$_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; (Ci-C$_6$)alkylthio can be methylthio, ethylthio, propylthio, isopropylthio, butylthio, isobutylthio, pentylthio, or hexylthio; (C2-C$_6$)alkanoyloxy can be acetoxy, propanoyloxy, butanoyloxy, isobutanoyloxy, pentanoyloxy, or hexanoyloxy.

As noted above, alkyl groups can be unsubstituted, Typical substituents include, but are not limited to, halo, =O, =N—CN, =N—OR$^a$, =NR$^a$—OR$^a$, —NR$^a_2$, —SR$^a$, —SO$_2$R$^a$, —SO$_2$NR$^a_2$, —NR$^a$SO$_2$R$^a$, —NR$^a$CONR$^a_2$, —NR$^a$COOR$^a$, —NR$^a$COR$^a$, —CN, —COOR$^a$, —CONR$^a_2$, —OOCR$^a$, —COR$^a$, and —NO$_2$, wherein each R$^a$ is independently H, C1-C8 alkyl, C2-C8 heteroalkyl, C3-C8 heterocyclyl, C4-C10 heterocyclyclalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R$^a$ is optionally substituted with halo, =O, =N—CN, =N—OR$^b$, =NR$^b$OR$^b$, NR$^b_2$, SR$^b$, SO$_2$R$^b$, SO$_2$NR$^b_2$, NR$^b$SO$_2$R$^b$, NR$^b$CONR$^b_2$, NR$^b$CO-OR$^b$, NR$^b$COR$^b$, CN, COOR$^b$, CONR$^b_2$, OOCR$^b$, COR$^b$, and NO$_2$, wherein each R$^b$ is independently H, C1-C8 alkyl, C2-C8 heteroalkyl, C3-C8 heterocyclyl, C4-C10 heterocyclyclalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group. Where a substituent group contains two R$^a$ or R$^b$ groups on the same or adjacent atoms (e.g., —NR$^b_2$, or NR$^b$—C(O)R$^b$), the two R$^a$ or R$^b$ groups can optionally be taken together with the atoms in the substituent group to which are attached to form a ring having 5-8 ring members, which can be substituted as allowed for the R$^a$ or R$^b$ itself, and can contain an additional heteroatom (N, O or S) as a ring member.

The term "alkenyl" as used herein refers to an alkyl as defined above having at least two carbon atoms and at least one carbon-carbon double bond. Thus, particularly contemplated alkenyl groups include straight, branched, or cyclic alkenyl groups having two to ten carbon atoms (e.g., ethenyl, propenyl, butenyl, pentenyl, etc.) or 5-10 atoms for cyclic alkenyl groups. Alkenyl groups are optionally substituted by groups suitable for alkyl groups as set forth herein. Similarly, the term "alkynyl" as used herein refers to an alkyl or alkenyl as defined above and having at least two (preferably three) carbon atoms and at least one carbon-carbon triple bond. Especially contemplated alkynyls include straight, branched, or cyclic alkynes having two to ten total carbon atoms (e.g., ethynyl, propynyl, butynyl, cyclopropylethynyl, etc.). Alkynyl groups are optionally substituted by groups suitable for alkyl groups as set forth herein.

The term "cycloalkyl" as used herein refers to a cyclic alkane (i.e., in which a chain of carbon atoms of a hydrocarbon forms a ring), preferably including three to eight carbon atoms. Thus, exemplary cycloalkanes include cyclopropyl, cyclobutyl, cyclopentyl, cyclohexyl, cycloheptyl, and cyclooctyl. Cycloalkyls also include one or two double bonds, which form the "cycloalkenyl" groups. Cycloalkyl groups are optionally substituted by groups suitable for alkyl groups as set forth herein.

"Carbocyclyl," "carbocyclic ring" or "carbocycle" refers to a rings structure, wherein the atoms which form the ring are each carbon, and which is attached to the rest of the molecule by a single bond. Carbocyclic rings can comprise from 3 to 20 carbon atoms in the ring. Carbocyclic rings include aryls and cycloalkyl, cycloalkenyl, and cycloalkynyl as defined herein. Unless stated otherwise specifically in the specification, a carbocyclyl group can be optionally substituted.

"Cycloalkenyl" refers to a stable non-aromatic monocyclic or polycyclic hydrocarbon consisting solely of carbon and hydrogen atoms, having one or more carbon-carbon double bonds, which can include fused or bridged ring systems, having from three to twenty carbon atoms, preferably having from three to ten carbon atoms, and which is attached to the rest of the molecule by a single bond. Monocyclic cycloalkenyls include, for example, cyclopentenyl, cyclohexenyl, cycloheptenyl, cyclooctenyl, and the like. Polycyclic cycloalkenyls include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon consisting solely of carbon and hydrogen atoms, having one or more carbon-carbon triple bonds, which can include fused or bridged ring systems, having from three to twenty carbon atoms, preferably having from three to ten carbon atoms, and which is attached to the rest of the molecule by a single bond. Monocyclic cycloalkynyl include, for example, cycloheptynyl, cyclooctynyl, and the like. Unless otherwise stated specifically in the specification, a cycloalkynyl group can be optionally substituted.

"Heterocyclyl," "heterocyclic ring" or "heterocycle" refers to a stable saturated, unsaturated, or aromatic 3- to 20-membered ring which consists of two to nineteen carbon atoms and from one to six heteroatoms selected from the group consisting of nitrogen, oxygen and sulfur, and which is attached to the rest of the molecule by a single bond. Heterocyclyl or heterocyclic rings include heteroaryls, heterocyclylalkyls, heterocyclylalkenyls, and hetercyclylalkynyls. Unless stated otherwise specifically in the specification, the heterocyclyl can be a monocyclic, bicyclic, tricyclic or tetracyclic ring system, which can include fused, bridged, or spirocyclic ring systems; and the nitrogen, carbon or sulfur atoms in the heterocyclyl can be optionally oxidized; the nitrogen atom can be optionally quaternized; and the heterocyclyl can be partially or fully saturated. Examples of such heterocyclyl include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2 oxopiperazinyl, 2 oxopiperidinyl, 2 oxopyrrolidinyl, oxazolidinyl, piperidinyl, piperazinyl, 4 piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1 oxo thiomorpholinyl, and 1,1 dioxo thiomorpholinyl. Unless stated otherwise specifically in the specification, a heterocyclyl group can be optionally substituted.

The term "aryl" or "aromatic moiety" as used herein refers to an aromatic ring system, which may further include one or more non-carbon atoms. These are typically 5-6 membered isolated rings, or 8-10 membered bicyclic groups, and can be substituted. Thus, contemplated aryl groups include (e.g., phenyl, naphthyl, etc.) and pyridyl. Further contemplated aryl groups may be fused (i.e., covalently bound with 2 atoms on the first aromatic ring) with one or two 5- or 6-membered aryl or heterocyclic group and are thus termed "fused aryl" or "fused aromatic".

Aromatic groups containing one or more heteroatoms (typically N, O or S) as ring members can be referred to as heteroaryl or heteroaromatic groups. Typical heteroaromatic groups include monocyclic C5-C6 aromatic groups such as pyridyl, pyrimidyl, pyrazinyl, thienyl, furanyl, pyrrolyl, pyrazolyl, thiazolyl, oxazolyl, isothiazolyl, isoxazolyl, and imidazolyl and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, pyrazolopyrimidyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms.

As also used herein, the terms "heterocycle", "cycloheteroalkyl", and "heterocyclic moieties" are used interchangeably herein and refer to any compound in which a plurality of atoms form a ring via a plurality of covalent bonds, wherein the ring includes at least one atom other than a carbon atom as a ring member. Particularly contemplated heterocyclic rings include 5- and 6-membered rings with nitrogen, sulfur, or oxygen as the non-carbon atom (e.g., imidazole, pyrrole, triazole, dihydropyrimidine, indole, pyridine, thiazole, tetrazole etc.). Typically, these rings contain 0-1 oxygen or sulfur atoms, at least one and typically 2-3 carbon atoms, and up to four nitrogen atoms as ring members. Further contemplated heterocycles may be fused (i.e., covalently bound with two atoms on the first heterocyclic ring) to one or two carbocyclic rings or heterocycles and are thus termed "fused heterocycle" or "fused heterocyclic ring" or "fused heterocyclic moieties" as used herein. Where the ring is aromatic, these can be referred to herein as 'heteroaryl' or heteroaromatic groups.

Heterocyclic groups that are not aromatic can be substituted with groups suitable for alkyl group substituents, as set forth above.

Aryl and heteroaryl groups can be substituted where permitted. Suitable substituents include, but are not limited to, halo, —OR$^a$, —NR$^a{}_2$, —SR$^a$, —SO$_2$R$^a$, —SO$_2$NR$^a{}_2$, —NR$^a$SO$_2$R$^a$, —NR$^a$CONR$^a{}_2$, —NR$^a$COOR$^a$, —NR$^a$COR$^a$, —CN, —COOR$^a$, —CONR$^a{}_2$, —OOCR$^a$, —COR$^a$, and —NO$_2$, wherein each Reis independently H, C1-C8 alkyl, C2-C8 heteroalkyl, C3-C8 heterocyclyl, C4-C10 heterocyclyclalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R$^a$ is optionally substituted with halo, =O, =I, =N—CN, N—OR$^b$, —N—R$^b$, OR$^b$, NR$^b_2$, SR$^b$, SO$_2$R$^b$, SO$_2$NR$^b_2$, NR$^b$SO$_2$R$^b$, NR$^b$CONR$^b_2$, NR$^b$COOR$^b$, NR$^b$COR$^b$, CN, COOR$^b$, CONR$^b_2$, OOCR$^b$, COR$^b$, and NO$_2$, wherein each R$^b$ is independently H, C1-C8 alkyl, C2-C8 heteroalkyl, C3-C8 heterocyclyl, C4-C10 heterocyclylalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group. Where a substituent group contains two R$^a$ or R$^b$ groups on the same or adjacent atoms (e.g., —NR$^b_2$, or NR$^b$—C(O)R$^b$), the two R$^a$ or R$^b$ groups can optionally be taken together with the atoms in the substituent group to which are attached to form a ring having 5-8 ring members, which can be substituted as allowed for the R$^a$ or R$^b$ itself, and can contain an additional heteroatom (N, O or S) as a ring member.

"Aryloxy" means a moiety of the formula —OR, wherein R is an aryl moiety as defined herein.

"Arylalkyl" and "Aralkyl", which may be used interchangeably, mean a radical-R$^a$R$^b$ where R$^a$ is an alkylene group and R$^b$ is an aryl group as defined herein; e.g., phenylalkyls such as benzyl, phenylethyl, 3-(3-chlorophenyl)-2-methylpentyl, and the like are examples of arylalkyl.

The term "alkoxy" as used herein refers to a hydrocarbon group connected through an oxygen atom, e.g., —O-Hc, wherein the hydrocarbon portion Hc may have any number of carbon atoms, typically 1-10 carbon atoms, may further include a double or triple bond and may include one or two oxygen, sulfur or nitrogen atoms in the alkyl chains, and can be substituted with aryl, heteroaryl, cycloalkyl, and/or heterocyclyl groups. For example, suitable alkoxy groups include methoxy, ethoxy, propyloxy, isopropoxy, methoxyethoxy, benzyloxy, allyloxy, and the like. Similarly, the term "alkylthio" refers to alkylsulfides of the general formula —S-Hc, wherein the hydrocarbon portion Hc is as described for alkoxy groups. For example, contemplated alkylthio groups include methylthio, ethylthio, isopropylthio, methoxyethylthio, benzylthio, allylthio, and the like.

The term 'amino' as used herein refers to the group —NH$_2$. The term "alkylamino" refers to amino groups where one or both hydrogen atoms are replaced by a hydrocarbon group Hc as described above, wherein the amino nitrogen "N" can be substituted by one or two Hc groups as set forth for alkoxy groups described above. Exemplary alkylamino groups include methylamino, dimethylamino, ethylamino, diethylamino, etc. Also, the term "substituted amino" refers to amino groups where one or both hydrogen atoms are replaced by a hydrocarbon group Hc as described above, wherein the amino nitrogen "N" can be substituted by one or two Hc groups as set forth for alkoxy groups described above.

As used herein, a "heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, thiophenyl, furanyl, pyranyl, pyridinyl, pyrrolyl, pyrazolyl, pyrimidyl, quinolinyl, isoquinolinyl, benzofuryl, benzofuranyl, benzothiophenyl, benzothiopyranyl, benzimidazolyl, benzoxazolyl, benzoxadiazolyl, benzothiazolyl, benzothiadiazolyl, benzopyranyl, indolyl, indazolyl, azaindolyl. pyrrolopyridine, pyrrolopyrimidine, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof. "Heteroarylalkyl" and "heteroaralkyl", which may be used interchangeably, mean a radical-R'R$^b$ where R$^a$ is an alkylene group and R$^b$ is a heteroaryl group as defined herein.

The term "aliphatic" as applied to cyclic groups refers to ring structures in which any double bonds that are present in the ring are not conjugated around the entire ring structure.

The term "aromatic" as applied to cyclic groups refers to ring structures which contain double bonds that are conjugated around the entire ring structure, possibly through a heteroatom such as an oxygen atom or a nitrogen atom. Aryl groups, pyridyl groups and furan groups are examples of aromatic groups. The conjugated system of an aromatic group contains a characteristic number of electrons, for example, 6 or 10 electrons that occupy the electronic orbitals making up the conjugated system, which are typically un-hybridized p-orbitals.

As used herein, "Azaindole" means a group of the formula

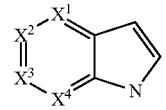

wherein one of X$^1$, X$^2$, X$^3$ and X$^4$ is N (aza), and the others are carbon. "Azaindoles" may be optionally substituted, as defined herein for heteroaryls, at position 1, 2 and 3, and at any of positions 4-through seven that are not nitrogen. "Azaindole" thus includes: "pyrrolopyridines" of the above formula wherein X$^1$ is N; "pyrrolopyridines" of the above formula wherein X$^2$ is N; "pyrrolopyridines" of the above formula wherein X$^3$ is N; and "pyrrolopyridines" of the above formula wherein X$^4$ is N;

As used herein, a "Pyrrolopyridine" may also mean a heteroaryl of the formula:

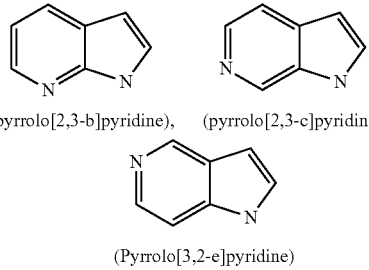

(pyrrolo[2,3-b]pyridine),   (pyrrolo[2,3-c]pyridine), or (Pyrrolo[3,2-e]pyridine)

In one example, a "Pyrrolopyridine" is an "azaindole" as defined herein.

In certain embodiments, the invention includes reacting a Pyrrolopyridine or a Azaindole, and preferably a 5-5 and 6-Azaindole analogs, with an electron releasing protection group, such as a benzyl group.

The hydrocarbon portion of each alkoxy, alkylthio, alkylamino, and aryloxy, etc. can be substituted as appropriate for the relevant hydrocarbon moiety.

The term "halogen" as used herein refers to fluorine, chlorine, bromine, and iodine. Where present as a substituent group, halogen or halo typically refers to F or Cl or Br, more typically F or Cl.

The term "haloalkyl" refers to an alkyl group as described above, wherein one or more hydrogen atoms on the alkyl group have been substituted with a halo group. Examples of such groups include, without limitation, fluoroalkyl groups, such as fluoroethyl, trifluoromethyl, difluoromethyl, trifluoroethyl and the like.

The term "haloalkoxy" refers to the group alkyl-O— wherein one or more hydrogen atoms on the alkyl group have been substituted with a halo group and include, by way of examples, groups such as trifluoromethoxy, and the like.

It should further be recognized that all of the above-defined groups may further be substituted with one or more substituents, which may in turn be substituted with hydroxy, amino, cyano, C1-C4 alkyl, halo, or C1-C4 haloalkyl. For example, a hydrogen atom in an alkyl or aryl can be replaced by an amino, halo or C1-4 haloalkyl or alkyl group.

The term "substituted" as used herein refers to a replacement of a hydrogen atom of the unsubstituted group with a functional group, and particularly contemplated functional groups include nucleophilic groups (e.g., —NH$_2$, —OH, —SH, —CN, etc.), electrophilic groups (e.g., C(O)OR, C(X)OH, etc.), polar groups (e.g., —OH), non-polar groups (e.g., heterocycle, aryl, alkyl, alkenyl, alkynyl, etc.), ionic groups (e.g., —NH3+), and halogens (e.g., —F, —Cl), NHCOR, NHCONH$_2$, OCH$_2$COOH, OCH$_2$CONH$_2$, OCH$_2$CONHR, NHCH$_2$COOH, NHCH$_2$CONH$_2$, NHSO$_2$R, OCH$_2$-heterocycles, PO$_3$H, SO$_3$H, amino acids, and all chemically reasonable combinations thereof. Moreover, the term "substituted" also includes multiple degrees of substitution, and where multiple substituents are disclosed or claimed, the substituted compound can be independently substituted by one or more of the disclosed or claimed substituent moieties. In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, compounds arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

As used herein, substituted with reference to an acyl, or a "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

As used herein and unless otherwise indicated, the term "glucuronide" means a compound bearing a glycoside of glucuronic acid, having a general formula:

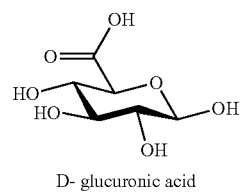

D- glucuronic acid

The term "modulation" as used herein in the context of serotonin, or other receptor binding, refers to a change in activation state as compared to the absence of a compound of the invention, or a patent compound of one or more of the compounds of the invention.

The term "beneficial" as used herein in the context of treating a condition, refers to extended relieve of symptoms (duration) and/or a more significant reduction of symptoms (magnitude).

As used herein, "lipophilicity" refers to the tendency of a compound to partition between a lipophilic organic phase and a polar aqueous phase. In drug development lipophilicity of a compound is represented either as partition coefficient, log P or distribution coefficient, log D.

As used herein, a "therapeutically effective amount" for treating "a disease or condition for which modulation of serotonin receptor activity is beneficial" may include, but not be limited to: for schizophrenia, a therapeutically effective amount is an amount which causes a significant reduction in psychopathology as determined by clinical improvement; for depression, a therapeutically effective amount is an amount that leads to stabilization and remission of symptoms as measured by the Patient Health Questonnaire-9; for OCD, a therapeutically effective amount is an amount that leads to stabilization and remission of symptoms as measured by the Yale-Brown Obsessive Compulsive Scale; for ADHD, a therapeutically effective amount is an amount that leads to stabilization and remission of symptoms as measured by either the ADHD Rating Scale V or ADHD Self-Report Scale; for eating disorders, a therapeutically effective amount is an amount that leads to stabilization and remission of symptoms as measured by the Eating Disorder Examination Questionnaire; for autism spectrum disorders a therapeutically effective amount is an amount that leads to stabilization and remission of symptoms as measured by physicians' assessment for PTSD a therapeutically effective amount is an amount that leads to stabilization and remission of symptoms as measured by the Clinician-Administered PTSD Scale for DSM-5; for anxiety, a therapeutically effective amount is an amount that leads to stabilization and remission of symptoms as measured by the General Anxiety Disorder-7; for addiction, a therapeutically effective amount is an amount that leads to stabilization and remission of symptoms as measured by physicians' assessment; for cluster headaches, a therapeutically effective amount is an amount that leads to stabilization and remission of symptoms as measured by the Cluster Headache Severity Scale (CHSS); for dementia, a therapeutically effective amount is an amount that leads to stabilization and remission of symptoms as measured by the Dementia Rating Scale (DRS); for Alzheimer's disease, a therapeutically effective amount is an amount that leads to stabilization and remission of symptoms as measured by the Alzheimer's Disease Assessment Scale-Cognitive Subscale (ADAS-Cog); for paralysis, a therapeutically effective amount is an amount that leads to stabilization and remission of symptoms as measured by physicians' assessment.

The term "treatment", as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e., prophylaxis) is also included.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's Pharmaceutical Sciences, Mack Publishing Co., Easton, Pa. (19th Edition). The pharmaceutical acceptable carrier may comprise any conventional pharmaceutical carrier or excipient. The choice of carrier and/or excipient will to a large extent depend on factors such as the particular mode of administration, the effect of the carrier or excipient on solubility and stability, and the nature of the dosage form.

Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus, for oral administration, tablets containing various excipients, such as citric acid may be employed together with various disintegrants such as starch, alginic acid and certain complex silicates and with binding agents such as sucrose, gelatin and acacia. Examples, without limitation, of excipients include calcium carbonate, calcium phosphate, various sugars and types of starch, cellulose derivatives, gelatin, vegetable oils and polyethylene glycols. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The term "pharmaceutically acceptable salt" means a salt which is acceptable for administration to a patient, such as a mammal, such as human (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt. For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned above are meant to comprise the therapeutically active non-toxic acid and base addition salt forms which the compounds can form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic, and like acids. Conversely, these salt forms can be converted into the free base form by treatment with an appropriate base. The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g., the lithium, sodium, potassium, magnesium, calcium salts and the like, salts with organic bases, e.g., the benzathine, N-methyl-D-glucamine, hydrabamine salts, and salts with amino acids such as, for example, arginine, lysine, and the like.

What is claimed is:

1. A psilocin prodrug compound according to Formula I:

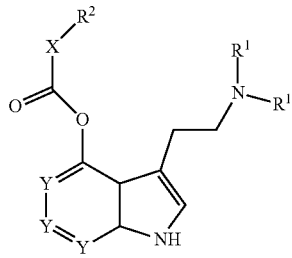

(I)

wherein,
Y is independently N or CH, wherein at least one Y is N;
X is O;
$R^1$ is $CH_3$, or $CH(CH_3)_2$; and
$R^2$ is $C_1$-$C_{14}$ linear alkane;
or a pharmaceutically acceptable salt thereof.

2. The compound of claim 1, wherein:
Y is independently N or CH, wherein at least one Y is N;
X is O;
$R^1$ is $CH_3$; and
$R^2$ is selected from methyl, ethyl, n-proply, n-butyl, n-pentyl, n-hexyl, n-heptyl, n-octyl, n-nonyl, n-decyl, n-undecanyl, n-dodecanyl, n-tridecanyl, n-tertadecanyl;
or a pharmaceutically acceptable salt thereof.

3. A psilocin prodrug compound according to Formula V:

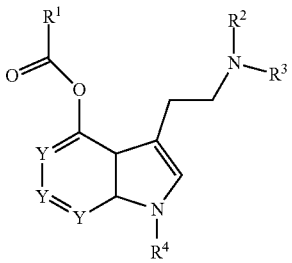

(V)

wherein,
Y is independently N or CH, wherein at least one Y is N;
$R^1$ is selected from —O—($C_{1-14}$ alkyl), —O—($C_{1-14}$ alkane), —O—$CH_2$-phenyl, —$CH_2$—$NH_2$, —CH(—$NH_2$)—$CH_3$, —CH(—$NH_2$)—CH($CH_3$)—$CH_3$, —CH(—$NH_2$)—$CH_2$—CH(—$CH_3$)—$CH_3$, —CH(—$NH_2$)—CH(—$CH_3$)—$CH_2CH_3$, —CH(—$NH_2$)—$CH_2CH_2$—$SCH_3$, —CH(—$NH_2$)—$CH_2$—SH, —CH(—$NH_2$)—$CH_2$—OH, —CH(—$NH_2$)—CH(—$CH_3$)—OH, —CH(—$NH_2$)—$CH_2$—C(=O)$NH_2$, —CH(—$NH_2$)—$CH_2CH_2$—C(=O)—$NH_2$, —CH(—$NH_2$)—$CH_2$—COOH, —CH(—$NH_2$)—$CH_2CH_2$—COOH, —CH(—$NH_2$)—$CH_2CH_2CH_2CH_2$—$NH_2$, —CH($NH_2$)—$CH_2CH_2CH_2$—NH—C(=NH)—$NH_2$, —CH(—$NH_2$)$CH_2$-(1H-imidazol-4-yl), —CH(—$NH_2$)—$CH_2$-(4-hydroxyphenyl), —CH(—$NH_2$)$CH_2$-(1H-indol-3-yl), -(pyrrolidin-2-yl), -(4-hydroxypyrrolidin-2-yl), —CH(—$NH_2$)—$CH_2$—S—S—$CH_2$—CH(—$NH_2$)—COOH, —CH(—$NH_2$)—$CH_2CH_2CH_2$—$NH_2$, —CH(—$NH_2$)—$CH_2CH_2CH_2$—NH—C(=O)—$NH_2$, —$CH_2$—$NHCH_3$, —CH(—$NH_2$)—$CH_2CH_2$—SH, —CH(—$NH_2$)—$CH_2CH_2$—OH, —CH(—$NH_2$)—$CH_2$-(3,4-dihydroxyphenyl), —CH(—$NH_2$)—$CH_2$-(5-hydroxy-1H-indol-3-yl), —$CH_2CH_2$—$NH_2$, —$CH_2CH_2CH_2$—$NH_2$, —CH(—$CH_3$)—$CH_2$—$NH_2$, —C(—$NH_2$)=$CH_2$, —O-(1-[$R^4$]-3-[(—$CH_2CH_2$—N(—$R^2$)—$R^3$)]-1H-indol-4-yl), —O($C_{1-14}$ alkylene)-O-(1-[$R^4$]-3-R—$CH_2CH_2$—N(—$R^2$)—$R^3$)]-1H-indol-4-yl), —CH(—$NH_2$)—$CH_2$—COO-(1-[$R^4$]-3-[($CH_2CH_2$—N(—$R^2$)—$R^3$)]-1H-indol-4-yl), —CH(—$NH_2$)—$CH_2CH_2$—COO-(1H-$R^4$-3-[(—$CH_2CH_2$—N(—$R^2$)—$R^3$)]-1H-indol-4-yl), —CH(—$NH_2$)—$CH_2$—S—S—$CH_2$—CH(—$NH_2$)—COO-(1-[$R^4$]-3-[(—$CH_2CH_2$—N(—$R^2$)—$R^3$)]-1H-indol-4-yl), —O-(5-aminomethyl)isoxazol-3-yl), and —CH(—$NH_2$)-(3-hydroxy-isoxazol-5-yl);
$R^2$ and $R^3$ are each independently selected from hydrogen, methyl, ethyl, $CH(CH_3)_2$ provided that $R^2$ and $R^3$ are not both hydrogen; and
$R^4$ is hydrogen or —C(=O)—O—(C1-6 alkyl);
or a pharmaceutically acceptable salt thereof.

4. The compound of claim 3, wherein $R^1$ is selected from —O—($C_{1-12}$ alkyl) or —O—$CH_2$-phenyl.

5. The compound of claim 3, wherein $R^1$ is selected from —$CH_2$—$NH_2$, —CH(—$NH_2$)$CH_3$, —CH(—$NH_2$)—CH(—$CH_3$)—$CH_3$, —CH(—$NH_2$)—$CH_2$—CH(—$CH_3$)—$CH_3$, —CH(—$NH_2$)—CH(—$CH_3$)$CH_2CH_3$, —CH(—$NH_2$)$CH_2CH_2$—S—$CH_3$, —CH(—$NH_2$)—$CH_2$—SH, —CH(—$NH_2$)—$CH_2$—OH, —CH(—$NH_2$)—CH(—$CH_3$)—OH, —CH(—$NH_2$)—$CH_2$—C(=O)$NH_2$, —CH(—$NH_2$)—$CH_2CH_2$—C(=O)—$NH_2$, —CH(—$NH_2$)—$CH_2$—COOH, —CH(—$NH_2$)—$CH_2CH_2$—COOH, —CH(—$NH_2$)—$CH_2CH_2CH_2CH_2$—$NH_2$, —CH(—$NH_2$)—$CH_2CH_2CH_2$—NH—C(=NH)—$NH_2$, —CH(—$NH_2$)—$CH_2$-(1H-imidazol-4-yl), —CH(—$NH_2$)—$CH_2$-phenyl, —CH(—$NH_2$)—$CH_2$-(4-hydroxyphenyl), —CH(—$NH_2$)—$CH_2$-(1H-indol-3-yl), and -(pyrrolidin-2-yl).

6. The compound of claim 3, wherein $R^1$ is selected from —CH(—$NH_2$)—CH(—$CH_3$)—$CH_3$, —CH($NH_2$)—$CH_2$—CH(—$CH_3$)—$CH_3$, —CH(—$NH_2$)—CH(—$CH_3$)$CH_2CH_3$, —CH(—$NH_2$)—$CH_2CH_2$—S—$CH_3$, —CH(—$NH_2$)—$CH_2$—SH, —CH(—$NH_2$)—$CH_2$—OH, —CH(—$NH_2$)—CH(—$CH_3$)—OH, —CH(—$NH_2$)—$CH_2$—C(=O)—$NH_2$, —CH(—$NH_2$)—$CH_2CH_2$—C(=O)$NH_2$, —CH(—$NH_2$)—$CH_2$—COOH, —CH(—$NH_2$)—$CH_2CH_2$—COOH, —CH(—$NH_2$)—$CH_2CH_2CH_2CH_2$—$NH_2$, —CH(—$NH_2$)$CH_2CH_2CH_2$—NH—C(=NH)—$NH_2$, —CH(—$NH_2$)—$CH_2$-(1H-imidazol-4-yl), —CH(—$NH_2$)—$CH_2$-phenyl, —CH(—$NH_2$)—$CH_2$-(4-hydroxyphenyl), —CH(—$NH_2$)—$CH_2$-(1H-indol-3-yl), and -(pyrrolidin-2-yl).

7. The compound of claim 3, wherein $R^1$ is selected from -(4-hydroxypyrrolidin-2-yl), —CH(—$NH_2$)—$CH_2$—S—S—$CH_2$—CH(—$NH_2$)—COOH, —CH(—$NH_2$)—$CH_2CH_2CH_2$—$NH_2$, —CH(—$NH_2$)—$CH_2CH_2CH_2$—NHC(=O)—$NH_2$, —$CH_2$—NH—$CH_3$, —CH(—$NH_2$)—$CH_2CH_2$—SH, —CH(—$NH_2$)—$CH_2CH_2$—OH, —CH(—$NH_2$)—$CH_2$-(3,4-dihydroxyphenyl), —CH(—$NH_2$)—$CH_2$-(5-hydroxy-1H-indol-3-yl), —$CH_2CH_2$—$NH_2$, —$CH_2CH_2CH_2$—$NH_2$, —CH(—$CH_3$)$CH_2$—$NH_2$, and —C(—$NH_2$)=$CH_2$.

8. The compound of claim 3, wherein $R^2$ and $R^3$ are each methyl.

9. The compound of claim 3, wherein $R^2$ is methyl and $R^3$ is hydrogen.

10. The compound of claim 3, wherein $R^2$ is methyl and $R^3$ is ethyl.

11. The compound of claim 3, wherein $R^4$ is hydrogen.

12. The compound of claim 3, wherein $R^4$ is —C(=O)—O—(C2-4 alkyl).

13. A psilocin prodrug compound selected from:

(Formula X)

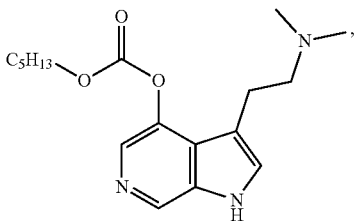

(Formula XI)

a pharmaceutically acceptable salt thereof.

14. A pharmaceutical composition comprising a compound of claim 1, and at least one pharmaceutically acceptable carrier.

15. A pharmaceutical composition comprising a compound of claim 3, and at least one pharmaceutically acceptable carrier.

16. A pharmaceutical composition comprising at least one compound of claim 13, and at least one pharmaceutically acceptable carrier.

* * * * *